United States Patent [19]

Nakayama et al.

[11] Patent Number: 5,264,559
[45] Date of Patent: Nov. 23, 1993

[54] AZOXY COMPOUNDS

[75] Inventors: Masahito Nakayama, Kodaira; Takeo Deushi, Sayama; Yoshio Takahashi, Iruma; Hiroyuki Ishiwata, Ichikawa; Yukihiro Okuno, Higashimurayama; Hisakatsu Itoh, Kwagoe; Masami Shiratsuchi, Musashimurayama, all of Japan

[73] Assignee: Kowa Company Ltd., Aichi, Japan

[21] Appl. No.: 656,829

[22] Filed: Feb. 19, 1991

[30] Foreign Application Priority Data

Feb. 19, 1990 [JP] Japan .................... 2-36339
Oct. 1, 1990 [JP] Japan .................... 2-260609

[51] Int. Cl.$^5$ .................. A01N 51/00; C07C 291/08
[52] U.S. Cl. .................. 534/566
[58] Field of Search ........... 534/566, 572; 514/720, 514/858, 149

[56] References Cited

U.S. PATENT DOCUMENTS

| | | | |
|---|---|---|---|
| 3,318,765 | 5/1967 | Fielding et al. | 514/720 |
| 3,647,776 | 3/1972 | McGohren et al. | 260/143 |
| 4,870,064 | 9/1989 | Takahashi et al. | 514/720 |
| 4,981,954 | 1/1991 | Nakayama et al. | 514/149 |

FOREIGN PATENT DOCUMENTS 0282001 9/1988 European Pat. Off. .
0396679 11/1990 European Pat. Off. .

OTHER PUBLICATIONS

Chemical Abstracts 108:182220a, abstracting FR 2,598,408, (1988).
Chemical Abstracts 68:68693n, abstracting JP 42011734, (1968).

*Primary Examiner*—Allen J. Robinson
*Assistant Examiner*—John D. Pak
*Attorney, Agent, or Firm*—Wenderoth, Lind & Ponack

[57] ABSTRACT

A compound expressed by the formula:

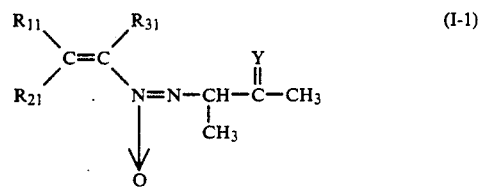

in which $R_{11}$, $R_{21}$ and $R_{31}$ are identical with or different from each other and each denotes a hydrogen atom, a halogen atom, an alkyl group, an alkenyl group, a haloalkyl group, an alkoxy group, an alkylthio group, an aryl or an aralkyl group which aromatic ring is optionally substituted appropriately by one to three substituents or a heterocyclic group optionally substituted appropriately by one to three substituents, or $R_{11}$ and $R_{21}$ may together form an alkylene group, Y denotes O or NOH, with a proviso that where $R_{21}$ (or $R_{11}$) and $R_{31}$ denote a hydrogen atom at the same time, $R_{11}$ (or $R_{21}$) cannot represent an n-butyl group. This compound is useful as an antifungal agent.

2 Claims, No Drawings

AZOXY COMPOUNDS

The present invention relates to azoxy compounds having antifungal activities. More specifically, the invention is concerned with a process for the preparation of a series of azoxy compounds containing antifungal substance KA-7367A which are expressed by the formula:

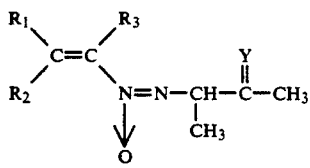
(I)

in which $R_1$, $R_2$ and $R_3$ are identical with or different from each other and each denotes a hydrogen atom, a halogen atom, an alkyl group, an alkenyl group, a haloalkyl group, an alkoxy group, an alkylthio group, an aryl or an aralkyl group which aromatic ring is optionally substituted appropriately by one to three substituents or a heterocyclic group optionally substituted appropriately by one to three substituents, or $R_1$ and $R_2$ may together form an alkylene group, Y denotes O or NOH, a new azoxy compound of the above formula (I) excluding antifungal substance KA-7367 and its use as an antifungal agent.

The Inventors previously discovered that Streptomyces s.p.KC-7367 (FERM BP-1277) separated from the soil in Maniwagun, Okayama Prefecture, Japan, would produce substances having a strong antifungal activities. Further, they isolated two kinds of antifungal substance KA-7367A (Maniwamycin A) and antifungal substance KA-7367B (Maniwamycin B) from its culture filtrate and identified these substances (see an official gazette of Tokkai Hei 1-6248).

The above antifungal substances KA-7367A and KA-7367B are expressed by the formula:

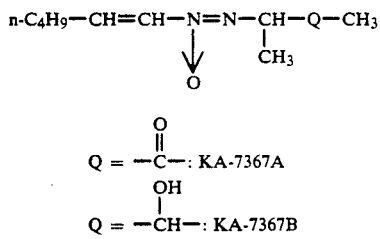

Further, the Inventors confirmed that 2-imino derivatives obtained by using KA-7367A as a raw material and then converting a carbonyl group at the second position of KA-7367A into an imino would exhibit superior antifungal activity and stability and disclosed its fact previously (WO90/04585).

These compounds display excellent antifungal activities and stability. However, in order to apply this to the therapy of dermatomycosis such as trichophytia they need a compound having a superior antitrichophytic activity.

Moreover, in order to obtain a compound having a superior antifungicidal activity it is further necessary to synthesize many derivatives and check their activities. The synthesisis of derivatives by using KA-7367 which is produced in accordance with the fermentation method as a raw material will involve such disadvatage that there is a restriction on the productivity of the raw material and the kind of derivative.

In an attempt to dissolve the above problem the Inventors made ardent studies by aiming at the production of KA-7376A depending on the organic synthesis method. As a result, they were successful in establishing an organic synthesis method of KA-7376A and its analogous substances. Further, they discovered that said analogous substances would be useful as an antifungal agents. This discovery led to the completion of the present invention.

Thus, according to one aspect of the present invention, there is provided a process for the preparation of compounds of the above formula (I) which comprises treating a compound of the formula (II):

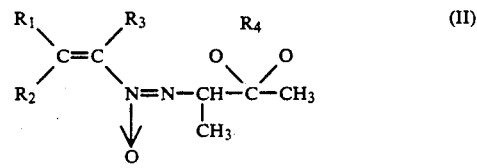
(II)

in which $R_1$, $R_2$ and $R_3$ have the above definitions and $R_4$ denotes a $C_2$–$C_6$ alkylene group, with an acid, reacting the resultant compound of the formula (I-2):

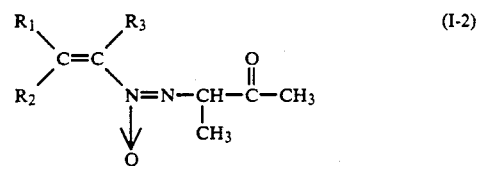
(I-2)

in which $R_1$, $R_2$ and $R_3$ have the above definitions, with hydroxylamine or its salt as required thereby to produce a compound of the formula (I-3):

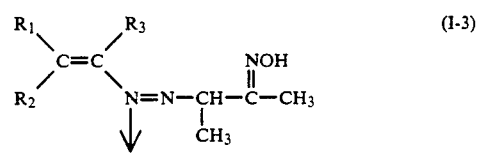
(I-3)

in which $R_1$, $R_2$ and $R_3$ have the above definitions.

Among the azoxy compounds of the above formula (I) produced by the above process of the present invention the following compounds are new ones not mentioned in the conventional literatures, i.e. compounds excluding KA-7367A and its 2-hydroxyimino derivative [a compound wherein $R_1$ (or $R_2$)=n-$C_4H_9$, $R_2$ (or $R_1$) and $R_3$=H].

Accordingly, in another aspect of the present invention, there is provided a compound of the formula (I-1):

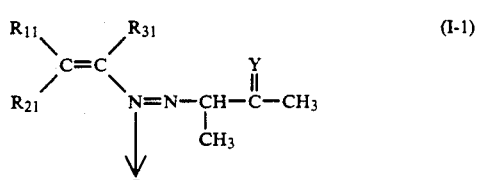
(I-1)

in which $R_{11}$, $R_{21}$ and $R_{31}$ are identical with or different from each other and each denotes a hydrogen atom, a halogen atom, an alkyl group, an alkenyl group, a haloalkyl group, an alkoxy group, an alkylthio group, an aryl or aralkyl group which aromatic ring is optionally substituted appropriately by one to three substituents or a heterocyclic group optionally substituted appropriately by one to three substituents, or $R_{11}$ and $R_{21}$ may together form an alkylene group, Y denotes O or NOH, with a proviso that where $R_{21}$ (or $R_{11}$) and $R_{31}$ denote a hydrogen atom at the same time $R_{11}$ (or $R_{21}$) cannot represent an n-butyl group.

The azoxy compound of the above formula (I-1) has an excellent antifungal activity and can expect to be used as an antifungal agent.

In the above formulae the "halogen atom" includes a fluorine atom, a chlorine atom, a bromine atom and an iodine atom.

The "alkyl group" here is optionally in the form of a straight chain or a branched chain. And its example may include methyl, ethyl, n- or iso-propyl, n-, -iso, sec- or tert-butyl, n-penthyl, iso-pentyl, neo-pentyl, n-hexyl, n-heptyl, n-octyl, methylhexyl, ethylhexyl, propylhexyl, methyldecanyl, ethyldecanyl, n-decanyl, n-dodecanyl, etc. In general, preferable is the one containing 1 to 12 carbon atoms.

The "alkenyl group" is also optionally in the form of a straight chain or a branched chain. And its example may include vinyl, allyl, propenyl, pentenyl, pentadienyl, isopropenyl, hexenyl, methylhexenyl, dimethylhexadienyl, hexatrienyl, etc. In particular, preferable is the one containing two to six carbon atoms.

The "alkoxy group" and "alkylthio group" are an akly-O-group and an akly-S-group in which the alkyl moiety has the above meaning, respctively. Preferable are those in which the alkyl moiety has one to six carbon atoms. Specific examples of such alkoxy group and alkylthio group include methoxy, ethoxy, n- or iso-propoxy, n-, iso-, sec- or tert-buthoxy, methylthio, ethylthio, n- or iso-propylthio, n-, iso-, sec- or tert-buthylthio, etc.

The "haloalkyl group" is such that at least one of the hydrogen atoms in the alkyl group is substituted by a halogen atom. Generally, suitable is the one having one to six carbon atoms. Preferable specific examples of such haloalkyl group may include fluoromethyl, trifluoromethyl, heptafluoropropyl, chloropropyl, bromohexyl, etc.

The "aryl group" is optionally monocyclic or polycyclic. And its example may include phenyl, alpha- or beta-naphtyl, etc. Above all, a phenyl group is suitable.

The "aralkyl group" ia an alkyl group substituted by an aryl group which aryl moiety has the above meaning. It is preferable for the carbon number of the arkyl moiety to be generally 1-4. Specific examples of such aralkyl group may include benzyl, phenethyl, phenylpropyl, naphthylmethyl, naphthylethyl, naphthylpropyl, etc. In particular, benzyl and phenethyl are suitable. In addition, aromatic rings in the above aryl group and aralkyl group are optionally substituted appropriately by one to three substituents. Such substituent can be selected from a halogen atom, a $C_1-C_6$ alkyl group, a $C_1-C_{10}$ alkoxy group, a $C_2-C_{10}$ alkenyloxy group, a $C_2-C_{10}$ alkinyloxy group, a phenyl group, a $C_1-C_6$ haloalkyl group, a $C_2-C_{10}$ haloalkenyl group, $C_2-C_{10}$ haloalkinyl group, $C_2-C_{10}$ haloalkenylloxy group, $C_2-C_{10}$ haloalkinyloxy group a hydroxyl group, a cyano group, a nitro group, etc.

The "heterocyclic group" includes a 4–14 membered, preferably a 5–10-membered heterocyclic group containing one to three hetero atoms selected from an oxygen, a sulfur and a nitrogen atom. For example, can be given tetrahydropyraxyl, thianyl, piperidino, furyl, thienyl, pyrrolyl, piranyl, piridyl, oxazolyl, thiazolyl, pyrazolyl, pyrimidyl, quinazolinyl, indolyl etc. These heterocylic groups are optionally substituted by one to three substituents as mentioned above.

Furthermore, the "alkylene group" is optionally in the form of a straight chain or a branched chain. In particular, preferable is the one containing two to six carbon atoms. Concretely, can be given

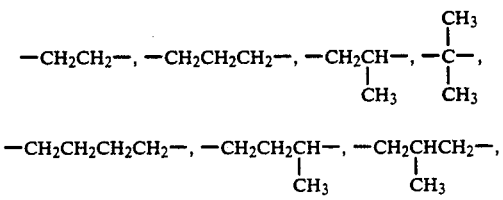

etc.

In the compounds of the above formula (I-1) provided by the present invention are included the following ones as an appropriate group of compounds, i.e. compounds in which the $R_{11}$, $R_{21}$ and $R_{31}$ are identical with or different from each other and each denotes a hydrogen atom, a $C_1-C_{10}$ alkyl group, a $C_2-C_3$ alkenyl group or a phenyl, benzyl or phenethyl group in which the benzene ring is optionally substituted appropriately by one or two substituents selected from a halogen atom, a phenyl group, a 3-halopropargyl group and a 3-halopropargyloxy group, or $R_{11}$ and $R_{21}$ may together form a $C_4-C_6$ alkylene group, with a proviso that where $R_{21}$ (or $R_{11}$) and $R_{31}$ are a hydrogen atom at the same time, $R_{11}$ (or $R_{21}$) cannot represent an n-butyl group. As another appropriate group of compounds can be given compounds of the formula (I-1) in which any one of $R_{11}$ and $R_{21}$ denotes a $C_1-C_{10}$ alkyl group, a $C_2-C_3$ alkenyl group or a phenyl, benzyl or phenethyl group which is optionally substituted appropriately by one or two substituents selected from a halogen atom, a phenyl group, a 3-halopropargyl group and a 3-halopropargyloxy group and the remainder denotes a hydrogen atom or a $C_1-C_6$ alkyl group, or $R_{11}$ and $R_{21}$ may together form a $C_4-C_6$ alkylene group, $R_{31}$ denotes a hydrogen atom, a $C_1-C_6$ alkyl group or a phenyl group which is optionally substituted appropriately by a halogen atom, with a proviso that where $R_{21}$ (or $R_{11}$) and $R_{31}$ represent a hydrogen atom at the same time, $R_{11}$ (or $R_{21}$) cannot represent an n-butyl group.

As a much more suitable group of compounds can be given 1-(1-propenyl-ONN-azoxy)-2-oxobutane, 3-(1-n-butenyl-ONN-azoxy)-2-oxobutane, 3-(1-n-pentenyl-ONN-azoxy)-2-oxobutane, 3-(1-n-heptenyl-ONN-azoxy)-2-oxobutane, 3-(1-n-nonenyl-ONN-azoxy)-2-oxobutane, 3-(1-n-decenyl-ONN-azoxy)-2-oxobutane, 3-(1,3-n-butadienyl-ONN-azoxy)-2-oxobutane, 3-(3-phenyl-1-propenyl-ONN-azoxy)-2-oxobutane, 3-(4-phenyl-1-butenyl-ONN-azoxy)-2-oxobutane, 3-(2-phenyl-1-propenyl-ONN-azoxy)-2-oxobutane, 3-(2-phenyl-1-butenyl-ONN-azoxy)-2-oxobutane, 3-(2-phenyl-1-pentenyl-ONN-azoxy)-2-oxobutane, 3-(2-phenyl-1-hexenyl-ONN-azoxy)-2-oxobutane, 3-[2-(p-chlorophenyl)-1-propenyl-ONN-azoxy]-2-oxobutane, 3-[2-(p-biphenyl)-1-propenyl-ONN-azoxy]-2-oxobutane, 3-[2-(2,4-dichlorophenyl)-1-pentenyl-ONN-azoxy]-2-oxobutane, 3-[2-(2,4-difluorophenyl)-1-propenyl-ONN-azoxyl-2-oxobutane, 3-[2-(p-chlorophenyl)-1-propenyl-ONN-azoxy]-2-oxobutane, 3-(1-methyl-1-hexenyl-ONN-azoxy)-2-oxobutane, 3-[cis-1(p-chlorophenyl)-1-hexenyl-ONN-azoxy]-2-oxobutane, 3-[trans-1(p-chlorophenyl)-1-hexenyl-ONN-azoxy]-2-oxobutane, 3-[3-(p-chlorophenyl)-2-buten-2-yl-ONN-azoxy]-2-oxobutane, 3-[7-(p-chlorophenyl)-6-octen-6-yl-ONN-azoxy]-2-oxobutane, 3-(6-undecen-6-yl-ONN-azoxy)-2-oxobutane, 3-(1-phenyl-1-hexenyl-ONN-azoxy)-2-oxobutane, 3-(1-cyclohexylidenemethyl-ONN-azoxy)-2-oxobutane, 2-hydroxyimino-3-[2-(4-(3-iodopropargyl)oxyphenyl)-1-propenyl-ONN-azoxy]-butane, 2-hydroxyimino-3-[2-(2-(3-iodopropargyl)oxyphenyl)-1-propenyl-ONN-azoxy]-butane, 2-hydroxyimino-3-[2-(3-(3-iodopropargyl)-1-propenyl-ONN-azoxy]-butane, 2-hydroxyimino-3-[2-(4-(3-iodopropargyl)oxyphenyl)-1-vinyl-ONN-azoxy]-butane, 3-[2-(2-chlorophenyl)-vinyl-ONN-azoxy]-2-hydroxyimino-butane, 3-[2-(2-chlorophenyl)-1-propenyl-ONN-azoxy]-2-hydroxyimino-butane, 3-[2-(2,4-dichlorophenyl)-1-propenyl-ONN-azoxy]-2-hydroxyimino-butane.

Shown below are other than those mentioned in the following working among specific examples of the compounds of the formula (I-1) provided by the present invention. 3-(2-ethoxyvinyl-ONN-azoxy)-2-oxobutane, 3-(2-methylthiovinyl-ONN-azoxy)-2-oxobutane, 3-(2,2-dimethylthiovinyl-ONN-azoxy)-2oxobutane, 3-(3,3,4,4,5,5,6,6-nonafluoro-1-hexenyl-ONN-azoxy)-2-oxobutane, 3-(3-phenyl-1-propenyl-ONN-azoxy)-2-oxobutane, 3-(3- -naphthyl-1-propenyl-ONN-azoxy)-2-oxobutane, 3-(4-tetrahydropyranyl-vinyl-ONN-azoxy)-2-oxobutane, 3-(4-tetrahydropyranyl-vinyl-ONN-azoxy)-2-oxobutane, 3-(2-furylvinyl-ONN-azoxy)-2-oxobutane, 3-(2-pyridylvinyl-ONN-azoxy)-2-oxobutane, 3-(2-quinazolinylvinyl-ONN-azoxy)-2-oxobutane, 2-hydroxyimino-3-(2-methoxyvinyl-ONN-azoxy)-butane, 3-(2-ethylthiovinyl-ONN-azoxy)-2-hydroxyimino-butane, 2-hydroxyimino-3-(2-methyl-2-methylthio-vinyl-ONN-azoxy)-butane, 3-(2,2-dichlorovinyl-ONN-azoxy)-2-hydroxyimino-butane, 2-hydroxyimino-3-(2-phenylvinyl-ONN-azoxy)-butane, 2-hydroxyimino-3-(4-propargylphenyl-vinyl-ONN-azoxy)-butane, 2-hydroxyimino-3-(2-thienylvinyl-ONN-azoxy)-butane, 3-[2-(3,5-dihydroxyphenyl)-1-propenyl-ONN-azoxy]-2-hydroxyimino-butane, 2-hydroxyimino-3-[2-(4-methoxypyridyl)-vinyl-ONN-azoxy)-butane, etc.

Where at least one of $R_1$ and $R_2$ or $R_{11}$ and $R_{21}$ represents a group having a definition other than the hydrogen atom in the above formula (I) or (I-1), two kinds of cis- and trans-type geometric isomers may exist in the compound of the formula (I) or (I-1). However, it should be understood that both of these two kinds of geometric isomers be included in the above formulae (I) and (I-1).

Further, the compound of the formula (I) or (I-1) contains an asymmetric carbon atom. Accordingly, said compound can exist in an optically active form or in the form of a mixture (e.g. a racemic form) of optically active isomers.

Furthermore, the compound of formula (I) or (I-1) in which Y denotes NOH can exist in a syn-form or an anti-form or in the form of a mixture of these two forms having an optional proportion.

The compound of the above formula (I) including the compound of formula (I-1) discussed above can be chemically synthesized via the production route shown in the following equation A, according to the process provided by the present invention:

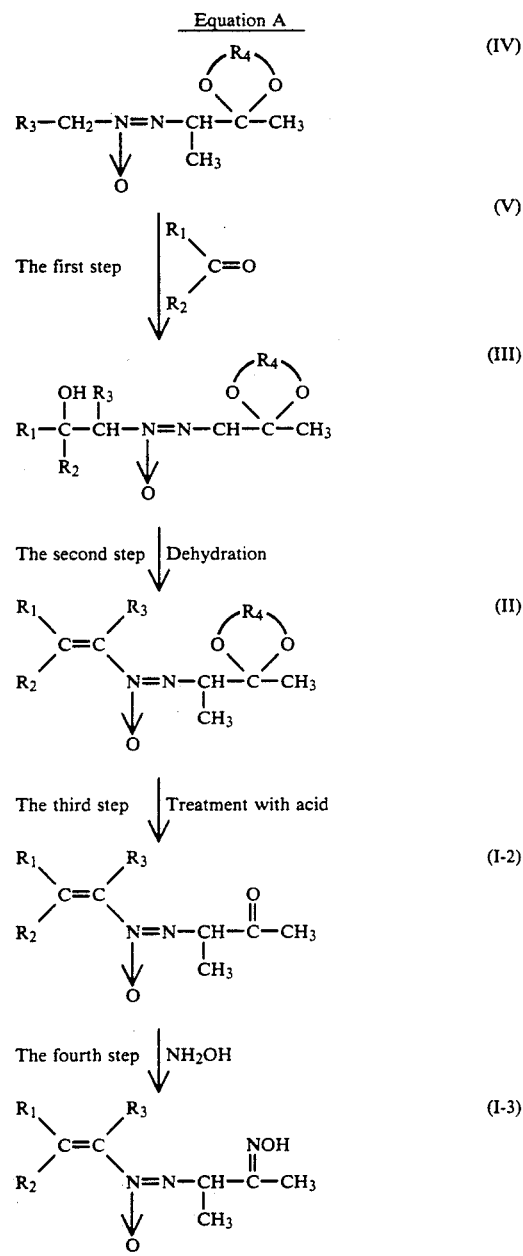

In the above equation $R_4$ denotes a $C_2$–$C_6$ alkylene group, preferably a $C_2$ or $C_3$ alkylene group, and $R_1$, $R_2$ and $R_3$ have the above definitions.

The process shown in the above equation will be explained below in greater detail about each step.

First Step

In this step the compound of formula (III) is produced by reacting the compound of formula (IV) with the compound (aldehyde or ketone) of formula (V).

It is preferable that this reaction be carried out after treating the compound of formula (IV) with a strong base and activating a carbon atom to which $R_3$ is bound.

Examples of the strong base available may include lithium diisopropylamide, lithium hexamethyldisilazide, sodium hydride, etc. An amount of such base used is not strictly restricted and may be changed according to the kind of bases, etc. Generally, it is appropriate that the above strong base be used within a range of 1 to 10 moles, preferably 1 to 3 mols relative to one mol of the compound of formula (IV).

In the case of using lithium diisopropylamide as the base, for example, the above activation can be conducted by reacting the compound of formula (IV) preferably with a newly prepared base in the solvent at temperatures of about minus 20° C. to about 50° C. for several minutes to several hours. Examples of the solvent available here may include halogenated hydrocarbon such as chloroform or methylene chloride, hydrocarbon such as benzene, toluene, xylene or cyclohexane, ethers such as ether, dioxane or tetrahydrofuran.

The so obtained reaction mixture can be reacted by adding the aldehyde or ketone in formula (V) thereto directly. At the moment, an amount of the compound of formula (V) used is not especially restricted. In general, however, it is convenient that the compound of formula (V) be used relative to one mol of the compound of formula (IV) in a proportion of 1 to 10 mols, preferably 1 to 3 moles. Further, the reaction temperature can be brought to be a range of about minus 20° C. to about 50° C., as in the above way. In this temperature range the reaction can be finished usually in several minutes to several hours.

Second Step

The compound of formula (III) produced in the above step is successively dehydrated and a carbon-carbon double bond is formed between the carbon to which OH is bound and its adjacent carbon.

The dehydration of the compound of formula (III) can be conducted in the way known per se. For instance, can be given (a) a method by which a hydroxyl group in the compound of formula (III) is sulfonylated and then desulfonated, (b) a method by which a hydroxyl group in the compound of formula (III) is substituted by a halogen atom and then dehydrohalogenated, etc.

The sulfonylation of the compound of formula (III) in the above method (a) can be performed in accordance with the usual method for the sulfonylation of alcohol, for example, by reacting the compound of formula (III) with a reactive derivative (e.g. acid halide) of an organic sulfonic acid like alkyl sulfonate (e.g. methane sulfonate) or aryl sulfonate (e.g. benzene sulfonate, p-toluene sulfonate, etc.) appropriately in a suitable solvent in the presence of a base usually at temperatures of from about minus 20° C. to about 100° C., preferably about minus 20° C. to about 30° C. The above reactive derivative of the organic sulfonic acid can be employed generally in a range of 1 mol to 10 mols, especially 1 mol to 2 mols relative to one mol of the compound of formula (III).

As the base are preferable pyridine, triethylamine, sodium hydride, etc. These can be used in a proportion of 1 mol to 10 mols, preferably 1 mol to 3 mols relative to one mol of the compound of formula (III). As the solvent can be used the above substances or it is possible to let said base play a role as the solvent by using it in large excess.

The resultant sulfonylation product is industrially advantageous if treating this in the usual way and subjecting it to a successive sulfonic acid removal reaction without its purification. The sulfonic acid removal reaction can be conducted, for example, by reacting the sulfonylation product with a dehydration agent in any suitable solvent at temperatures in a range of about minus 20° C. to about 100° C. for one to fifty hours or so. As the dehydration agent can be given 1,8-diazabicyclo[5.4.0]-7-undecene, triethylamine, pyridine, etc. An amount of the dehydration agent used can be brought to be generally in a range of 0.7 mol to 100 mols, preferably 1 mol to 10 mols relative to one mol of the compound of formula (III). The solvent can be used by selecting it from the above types.

In the above method (b) chlorine, bromine, iodine or the like can be illustrated as a halogen atom substitutable by a hydroxyl group. As the halogenation agent for substituting the hydroxyl group in the compound of formula (III) by such halogen atom can be given thionyl halide (e.g. thionyl chloride or the like), phosphorus oxyhalide (e.g. phosphorus oxychloride or the like), etc. for example. These can be used generally in a range of 1 mol to 100 mols, preferably 1 mol to 3 mols relative to one mol of the compound of formula (III).

The reaction can be conducted by reacting the compound of formula (III) with a halogenation agent preferably in the presence of a base in any suitable solvent at temperatures of about minus 20° C. to about 50° C. for several minutes to several hours. As the base are preferable pyridine, triethylamine, etc. These can be used usually in a proportion of 1 to 100 mols, preferably 1 to 2 mols relative to one mol of the compound of formula (III).

The resultant halide is industrially advantageous if treating this in the usual way and subjecting it to a successive sulfonic acid removal reaction without its purification. The dehydrohalogenation reaction can be conducted, for example, by reacting the resultant halide with a dehydration agent in any solvent at temperatures of about minus 20° C. to about 100° C., preferably about minus 20° C. to about 30° C. for one to fifty hours or so. As the dehydration agent and solvent can be used the above types.

Third Step

The compound of formula (I-2) is obtained by treating the compound of formula (II) produced in the above way with an acid.

Examples of the acid usuable in the above acid treatment may include an inorganic acid such as hydrochloric acid or sulfuric acid, an organic acid such as acetic acid or p-toluene sulfonic acid, a Lewis acid such as ferric chloride-silica gel, a cation exchange resin such as Amberlist ® 15 (a product of Organo Company), etc. An amount of these acids used is not especially restricted used but generally they can be employed in a proportion of 0.01 mol to a large excess, preferably 0.1 to 1 mol relative to one mol of the compound of formula (II).

The above acid treatment can be usually conducted, for example, by reacting the compound of formula (III) with an acid in any suitable solvent at temperatures between about minus 20° C. and about 100° C., preferably about 0° C. to about 30° C. for several minutes to several hours. As the solvent can be used ketones such as acetone or methyl ethyl ketone, acetonitrile or the like in addition to the above types.

Fourth Step

The compound of formula (I-2) obtained in the above step can be converted into the compound of formula (I-3) by reacting it with hydroxylamine, as required.

This reaction can be conducted usually in any suitable solvent and in the presence of any suitable base in a temperature range of about minus 10° C. to the reflux temperature of the solvent, preferably about 5° C. to about 100° C. Examples of the solvent available here may include alcohols such as methanol, ethanol or isopropanol, halogenated hydrocarbon such as chloroform or methylene chloride, hydrocarbon such as benzene, toluene, xylene or cyclohexane, ethers such as ether, dioxane or tetrahydrofuran.

Further, examples of the base which is usable as required may include an inorganic base such as sodium hydroxide, potassium hydroxide, sodium carbonate or potassium carbonate, an organic base such as triethylamine, pyridine or 4-methylamino pyridine, etc. These bases can be used generally in a range of 0.1 to 100 equivalents, 1 to 100 equivalents relative to one mol of the compound (II) of formula (I-2). Moreover, hydroxylamine or its salt (e.g. hydrochloride) can be used generally in a range of 1 mol to 10 mols, preferably 1 mol to 2 mols relative to one mol of the compound of formula (I-2). The compound of formula (I-2), a starting compound in this reaction, can be subjected to this reaction directly without purification after the completion of the preceding step.

When one wishes to produce the compound of formula (I-2) or (I-3) wherein $R_1$, $R_2$ and/or $R_3$ denote(s) an aryl or an aralkyl group which aromatic ring is substituted by one to three substituents and at least one of these substituents is a 3-halopropargyl group or a 3-halopropargyloxy group in the above equation A, a corresponding starting material in which said substituent is a propargyl group or a propargyloxy group is used as required and its halogenation is conducted at any optional stage of the reaction or at the stage of the compound of formula (II), whereby the propargyl group or propargyloxy group can be converted into a 3-halopropargyl group or a 3-halopropargyloxy group. As said 3-halopropargyl group or 3-haloproparglyoxy group is suitable a 3-iodopropargyl group or a 3-iodopropargyloxy group.

The isolation and purification of the final compound can be carried out by methods known per se, e.g. chromatography (e.g. silica gel chromatography and silica gel preparative thin- layer chromatography), extraction, lyoplylization, distillation and crystallization.

The compound of formula (IV) which is used as a starting compound in the above equation A can be produced, for example, by converting alanine into ethyl carbamate with ethyl chloroformate, successively methylating this with methyl lithium to form ketone, protecting this ketone with ketal, converting this into nitro in accordance with the method of Moss et al [J. Org. Chem. 31 (1966) 1082] and reacting this with potassium t-butylate thereby to produce diazotate of the formula:

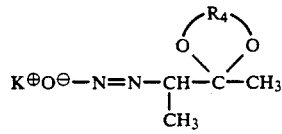

(VI)

wherein $R_4$ has the above definition, and reacting this with a compound of the formula $R_3$-$CH_2$-Hal (VII) in which Hal denotes a halogen atom and $R_3$ has the above definition.

The compound of formula (I) in this invention has high antifungal activity, and exhibits excellent antifungal activity to fungi that infect warm-blooded animals including human, such as Candida, Cryptococcus, Aspergillus, Trichophyton, etc. and fungi that infect agricultural and horticultural crops and fruit trees, such as Piricularia, Botrytis, Saccharomyces, Septoria, etc.

The minimum inhibitory concentrations (μg/ml), of the typical compounds in this invention produced in Examples to be described later were measured, and the results are tabulated below.

The minimum inhibitory concentrations were measured by an agar dilution method using a Sabouraud's dextrose medium in accordance with a standard method of Nippon Kagaku Ryoho Gakkai (Chemical Therapy Academy).

TABLE 1

| Test Compound (Example No.) | Minimum inhibitory concentration (μg/ml)* | | |
|---|---|---|---|
| | Test fungi | | |
| | Candida albicans | Trichophyton mentagrophytes | Trichophyton rubrum |
| 1 | 1.6 | 3.1 | 3.1 |
| 2 | 50 | 25 | 25 |
| 3 | 12.5 | 12.5 | 12.5 |
| 4 | 6.25 | 6.25 | 6.25 |
| 5 | 1.6 | 1.6 | 1.6 |
| 6 | 0.8 | 1.6 | 1.6 |
| 7 | 100 | 100 | 100 |
| 8 | 100 | 12.5 | 12.5 |
| 9 | 1.6 | 1.6 | 1.6 |
| 10 | 1.6 | 6.25 | 3.1 |
| 11 | 1.6 | 0.4 | 0.4 |
| 12 | 3.1 | 1.6 | 1.6 |
| 13 | 3.1 | 0.8 | 0.8 |
| 14 | 3.1 | 0.8 | 0.8 |
| 15 | 0.8 | 0.4 | 0.4 |
| 16 | 12.5 | 1.6 | 1.6 |
| 17 | 12.5 | 0.8 | 1.6 |
| 18 | 0.8 | 0.8 | 0.8 |
| 19 | 6.25 | 3.1 | 3.1 |
| 20 | 3.1 | 1.6 | 1.6 |
| 21 | 50 | 3.1 | 3.1 |
| 22 | 50 | 3.1 | 3.1 |
| 23 | 3.1 | 6.25 | 6.25 |
| 24 | 50 | 6.25 | 6.25 |
| 25 | 100 | 3.1 | 3.1 |
| 26 | 50 | 6.25 | 6.25 |
| 27 | 6.25 | 1.6 | 1.6 |
| 28 (anti) | 6.25 | 0.4 | 0.2 |
| (syn) | 3.1 | 0.8 | 0.2 |
| 29 (anti) | 12.5 | 0.8 | 0.2 |
| (syn) | 12.5 | 0.8 | 0.2 |
| 30 (anti) | 6.25 | 0.8 | 0.2 |
| (syn) | 6.25 | 0.8 | 0.4 |
| 31 (anti) | 6.25 | 0.4 | 0.1 |
| (syn) | 6.25 | 0.4 | 0.1 |
| 32 (mixture) | 12.5 | 1.6 | 1.6 |
| 33 (mixture) | 25 | 3.1 | 3.1 |
| 34 (mixture) | 12.5 | 3.1 | 3.1 |

As stated above, the compounds in this invention have excellent antifungal activity to fungi that infect warm-blooded animals including humans and fungi that infect agricultural and horticultural crops and fruit trees, and are useful as antifungal agents for medical, veterinary, agricultural and horticultural usages.

The compounds or their salts in this invention, when used as antifungal agents, can be prepared in dosage forms suited for various usages. For example, when the compounds or their salts in this invention are used as medicines or veterinary drugs (animal drugs), it is possible that adjuvants such as a vehicle, a binder, a lubricant, a disintegrator, a coating, an emulsifier, a suspending agent, a solvent, a stabilizer, an absorption aid, an ointment base, etc. can properly be added thereto and they are prepared into dosage forms for oral administration, administration by injection, subcutaneous injection and external use.

Examples of the preparations for oral administration are granules, tablets, sugar coated tablets, capsules, pills, liquid preparations, emulsions and suspensions. Examples of the preparations for administration by injection are preparations for intravenous injection, subcutaneous injection and instillation. Examples of the preparations for intrarectal administration are suppositories and soft elastic capsules. Examples of the preparations for external use are ointments, lotions, liniments and creams. Dosage forms such as eye drops, ear drops, etc. are also available.

The compounds or their salts in this invention, when used as agricultural and horticultural antifungal agents, can take dosage forms such as liquid preparations, emulsions, granules, powders, dusts and pastes.

The dose of the compound in this invention, when administered to the warm-blooded animals including humans, can vary over a wide range depending on types, conditions, weights and sexes of animals being administered, doctor's judgement, etc. Generally, it is about 0.1 to about 500 mg/kg.weight per day, and the compound can be administered either once or in divided portions a day.

When the compound in this invention is used as an agricultural and horticultural agent, it can be applied to a habitat area of fungi as an agent for soil treatment, an agent for treatment of stems and leaves, etc. Its dose can be e.g. about 0.005 to about 5 kg/ha.

The following Referential Examples, Examples and Preparation Examples illustrate this invention more specifically.

REFERENTIAL EXAMPLE 1

Production of 3-(methyl ONN azoxy)-2,2-propylene dioxy-butane [Compound (IV):$R_3$=H, $R_4$=-$CH_2CH_2CH_2$-]: (a) In 700 ml of water were dissolved 40 g of L-alanine and 127 g of sodium carbonate. Then 64 ml of ethyl chloroformate was added dropwise to the mixture under ice-cooling and its stirring was conducted at room temperature for 30 minutes. A 35% hydrochloric acid was added to the reaction liquid to make this acidic and the reaction liquid was adsorbed on the column (6.5×60 cm) of diaion HP-20. After washing with water this was eluted with 70% methanol. The eluate was condensed under vacuum thereby to obtain 69 g (yield of 96%) of N-ethoxycarbonyl alanine as an oily substance.

$^1$H-NMR value: $\delta CDCl_3$, ppm 1.26 (3H, t, J=7 Hz), 1.46 (3H, d, J=7 Hz), 4.15 (2H, q, J=7 Hz), 4.40 (1H, m), 5.28 (1H, br.d, J=7 Hz), 7.35 (1H, br.s).

IR value: $\gamma$maxm, $cm^{-1}$, 1719, 1697

(b) In 60 ml of tetrahydrofuran was dissolved 3 g of the N-ethoxycarbonyl alanine obtained by the above (a) in an atmosphere of nitrogen. While stirring the mixture vigorously at minus 78° C., 48 ml of a 1.19N methyl lithiusm ether solution for 30 minuites. Further, the mixture was stirred at the same temperature for 40 minutes and its stirring was conducted at room temperature for one hour. The reaction liquid was poured into a cooled 10% phosphoric acid solution and the extraction was conducted with ethyl acetate. The extraction liquid was washed with aqueous saturated sodium bicarbonate solution and then with water, dried and condensed under vacuum. The residue was purified by means of a silica gel column chromatography [solvent: chloroform-n-hexane (5:1)] thereby to produce 1.8 g (yield of 60%) of 3-ethoxycarbonylamino-2-oxobutane.

$^1$H-NMR value: $\delta CDCl_3$, ppm 1.24 (3H, t, J=7.0 Hz), 1.38 (3H, d, J=7.0 Hz), 2.20 (3H, s), 4.12 (2H, q, J=7.0 Hz), 4.37 (1H, br.t, J=7.0 Hz), 4.44 (1H, br.t) $CHCl_3$ IR value: $\gamma$max, $cm^{-1}$, 1706, 1500

(c) In 280 ml of benzene were dissolved 6.34 g of the ketone substance obtained by the above (b) and 500 mg of a pyridine salt of p-toluene sulfonic acid. To the mixture was added 22 ml of 1,3-propanediol and this was refluxed by heating it for four hours. After allowing the reaction liquid to cool, an aqueous saturated sodium bicarbonate solution was added to the reaction liquid and an organic layer was batched off. An aqueous layer was then extracted with benzene. The organic layer was concurrently condensed under vacuum. The residue was purified by means of a silica gel column chromatography [solvent: ether-n-hexane(1:3)] thereby to produce 8.25 g (yield of 95%) of 3-ethoxycarbonylamino-2,2-propylene oxobutane.

$^1$H-NMR value: $\delta CDCl_3$, ppm 1.17 (3H, d, J=7.0 Hz), 1.24 (3H, t, J=7.0 Hz), 1.37-1.50 (1H. m), 1.42 (3H, s), 1.80-2.02 (1H, m), 3.76-4.06 (5H, m), 4.11 (2H, q, J=7.0 Hz), 4.90 (1H, br.s), $CHCl_3$ IR value: $\gamma$max, $cm^{-1}$, 1701, 1507

(d) In 30 ml of an anhydrous ether was dissolved 4.49 g of the compound obtained by the above (c) in an atmosphere of nitrogen. Then 8.7 g of sodium bicarbonate was added to the mixture. This solution was cooled to minus 25° C. and 9.6 ml of an anydrous ether solution dissolving 3.3 ml of binitrogen tetroxide therein was added dropwise thereto. Its stirring was conducted at the same temperature for 3.5 hours. The reaction liquid was poured into the cooled aqueous saturated sodium bicarbonate solution, then extracted with ether. An ether layer was dried and condensed under vaccum at 30° C. or below, followed by removing water azeotropically.

Successively, 4.64 g of potassium t-buthoxide was suspended in 20 ml of dimethyl formamide and the suspension was cooled at minus 30° C. in an atmosphere of nitrogen. To this was added dropwise 6 ml of a dimethyl formamide solution dissolving the previously prepared N-nitroso compound therein. The mixture was stirred at minus 30° C. for 2.5 hours.

To this reaction liquid was added dropwise 6.44 ml of methyl iodide and the mixture was stirred at room temperature overnight. The reaction liquid was poured into a glacial water and an organic layer was extracted with ethyl acetate. After the orgnaic layer was dried, this was condensed under vacuum. The residue was purified by means of a silica gel column chromatography [solvent: ethyl acetate-n-hexane(1:3)]. The resultant residue was dissolved in 3 ml of pyridine and 1.5 ml of acetic anhydride as added to the mixture and its stirring was conducted at room temperature for one hour. The reaction liquid was poured into water and an organic layer was extracted with ethyl acetate. The orgnaic layer was dried over saturated sodium bicarbonate and condensed under vacuum. The residue was purified by means of a silica gel column chromatography [solvent: ethyl acetate-n-hexane(1:3)] thereby to produce 1.49 g (yield of 38% ) of an object compound.

$^1$H-NMR value: $\delta$CDCl3, ppm: 1.13 (3H, d, J=7.0 Hz), 1.45 (3H, s), 1.59-1.92 (2H, m), 3.85 (4H, m), 4.10 (3H, s, 4.49 (1H, q, J=7.0 Hz), CHCl3

IR value: $\gamma$max, cm$^{-1}$, 1503, 1424, 1370, 1330.

REFERENTIAL EXAMPLE 2

Production of 3-(ethyl-ONN-azoxy)-2,2-propyleneoxy butane [Compound (IV):$R_3$=CH3, $R_4$=-CH2CH2CH2-]:

In 50 ml of acetonitrile was dissolved 216 g of the 3-ethoxycarbonylamino-2,2-propylene dioxybutane obtained by referential Example 1-(c) and the mixture was cooled at minus 20° C. To this solution were added 1.6 ml of pyridine and 2.31 g of nitrosonium tetrafluoborate and the mixture was stirred for 25 minutes. Then the reaction liquid was poured into an aqueous mixture consisting of 250 ml of cooled methylne chloride and 100 ml of water and its stirring was conducted for ten minutes. An organic layer was washed with water, dried and condensed under vacuum. Benzene was added to the residue and water was removed therefrom azeotropically.

Successively, 1.52 g of potassium t-buthoxide was suspended in 200 ml of ether and the suspension was cooled at minus 35° C. in an atmosphere of nitrogen. To this was added dropwise 10 ml of an ether solution dissolving the above nitroso compound therein. The mixture was stirred at the same temperature for one hour and the reaction liquid condensed under vacuum.

The residue was dissolved in 10 ml of hexamethylphosphoric triamide and the mixture was cooled at 0° C. To this solution was added dropwise 3.8 ml of ethyl iodide and its stirring was conducted in a bath at 35° C. for 18 hours. The reaction liquid was poured into water and an organic layer was extracted with ether. After the orgnaic layer was dried, this was condensed under vacuum. The residue was purified by means of a silica gel column chromatography (solvent: chloroform) thereby to produce 495 mg (yield of 25% ) of an object compound.

$^1$H-NMR value: $\delta$CDCl3, ppm: 1.12 (3H, d, J=7.0 Hz), 1.45 (3H, s), 1.51 (3H, t, J=7.0 Hz), 3.87-4.00 (4H, m), 4.23 (2H, q, J=7.0 Hz), 4.53 (1H, q, J=7.0 Hz)

CHCl3

IR value: $\gamma$max, cm$^{-1}$, 1498

EXAMPLE 1

Production of 3-(1-hexenyl-ONN-azoxy)-2-oxobutane [KA-7367A, compound (I-2): $R_1$=n-butyl group, $R_2$=$R_3$=H]: (a) To 10 ml of a tetrahydrofuran solution dissolving lithium diisoproylamide therein, said lithium diisoproylamide being prepared from 0.536 ml of diisopropylamine and 2.39 ml of a 1.59N n-buthyl lithium hexane solution in an atmohspehre of nitrogen under ice-cooling, was added dropwise 549 mg of tetrahydrofuran dissolving 3-(methyl-ONN-azoxy)-2,2-propylene dioxybutane therein. Then 0.953 ml of n-valeraldehyde was added to this solution and its stirring was conducted for additional thirty minutes. An aqueous saturated ammonium chloride solution was added to the reaction liquid and an organic layer was extracted with ethyl acetate. This organic layer was washed with water, dried and condensed under vacuum. The residue was purified by means of a silica gel column chromatography [solvent: ethyl acetate-n-hexane(1:3)] thereby to produce 436 mg (yield of 54%) of 3-(2-hydroxyhexyl-ONN-azoxy)-2,2-propylene dioxybutane.

$^1$H-NMR value: $\delta$CDCl3, ppm, 0.90 (3H, br.t, J=8.0 Hz), 1.16, 1.18 (total 3H, each d, J=7.0 Hz), 1.24-1.94 (6H, m), 1.47 (3H, s), 3.66 (1H, br.s), 3.84-3.98 (4H, m), 4.0-4.37 (3H, m), 4.60 (1H, m).

CHCl3

IR value: $\gamma$max, cm$^{-1}$, 1497, 1370

(b) In 1.5 ml of pyridine was dissolved 160 mg of the 3-(2-hydroxyhexyl-ONN-azoxy)-2,2-propylene dioxybutane obtained by the above (a). Then 0.058 ml of methane sulfonyl chloride was added to the mixture under ice-cooling and its stirring was conducted at room temperature overnight. The reaction liquid was cooled at 0° C. and one drop of water was added to the reaction liquid. Its stirring was conducted at room temperature for thirty minutes. Further, 10 ml of water was adddded to the reaction liquid and an organic layer was extracted with ethyl acetate. This organic layer was washed with 0.5N hydrochloric acid and aqueous saturated sodium bicarbonate solution, dried and condensed under vacuum thereby to produce 220 mg of a crude methane sulfonyl compound.

This methane sulfonyl compound was dissolved in 2 ml of toluene and 0.14 ml of 1,8-diazabicyclo [5.4.0]-7-undecene was added to the mixture under ice-cooling. Its stirring was conducted at room temperature overnight. To the reaction liquid was added 10 ml of water and an organic layer was extracted with ethyl acetate. This organic layer was washed with 0.5N hydrochloric acid and aqueous saturated sodium bicarbonate solution, dried and condensed under vacuum. The residue was purified by means of a silica gel column chromatography [solvent: ether-n-hexane (1:5)] thereby to produce 133 mg (yield of 89%) of 3-(1-hexenyl-ONN-azoxy)-2,2-propylene dioxybutane.

$^1$H-NMR value: $\delta$CDCl3, ppm 0.90 (3H, t, J=7.0 Hz), 1.18 (3H, d, J=7.0 Hz), 1.22-1.53 (4H, m), 1.46 (3H, s), 1.56-1.68 (1H, m), 1.72-1.90 (1H, m), 2.12-2.26 (2H, m), 3.86-4.02 (4H, m), 4.64 (1H, q, J=7.0 Hz), 6.98 (2H, m).

CHCl3

IR value: $\gamma$max, cm$^{-1}$, 1405, 1380, 1316, 964

(c) In 3 ml of acetone was dissolved 80 mg of the 3-(1-hexenyl-ONN-azoxy)-2,2-propylene dioxybutane obtained by the above (b). Then 40 ml of ferric chloride-silca gel was added to the mixture and its stirring was conducted at room temperature for one hour. The reaction liquid was filtered with zeolite. Then 10 ml of water was added to the filtrate and an organic layer was extracted with ethyl acetate. This organic layer was washed with water and saturated saline solution, dried and condensed under vacuum. The residue was purified by means of a silicagel column chromatography [solvent: ether-n-hexane (1:5)] thereby to produce 31 mg (yield of 50%) of the captioned object compound (KA-7367A).

Specific optically rotation: $[\alpha]_D^{22}$ −160° (c 1.0, CHCl$_3$)

1H-NMR value: δCDCl3, ppm: 0.89 (3H, t, J=7.0 Hz), 1.27-1.48 (4H, m), 1.37 (3H, d, J=7.5 Hz), 1.22-1.53 (4H, m), 2.10 (3H, s), 2.22 (2H, brq, J=7.5 Hz), 4.52 (1H, q, J=7.5 Hz), 6.90 (1H, dt, J=14.0 Hz, 7.5 Hz), 7.23 (1H, dd, J=14.0 Hz, 1.0 Hz),
CHCl3
IR value: γmax, cm$^{-1}$, 1717, 1463

EXAMPLES 2–10

Using the corres. starting compound the reaction and treatment were made as in Example 1, thereby to produce the compound (I-2) shown in Table 2.

TABLE 2

R$_1$R$_3$C=C(R$_2$)—N=N(→O)—CH(CH$_3$)—C(=O)—CH$_3$  (I-2)

| Example No. | R$_1$ | R$_2$ | R$_3$ | $[\alpha]_D^{\prime\prime}$ (CHCl$_3$) |
|---|---|---|---|---|
| 2 | —CH$_3$ | H | H | −189° (c 0.3) |
| 3 | —CH$_2$CH$_3$ | H | H | −161° (c 1.0) |
| 4 | —(CH$_2$)$_2$CH$_3$ | H | H | −142° (c 1.0) |
| 5 | —(CH$_2$)$_4$CH$_3$ | H | H | −126° (c 1.0) |
| 6 | —(CH$_2$)$_6$CH$_3$ | H | H | −116° (c 1.0) |
| 7 | —(CH$_2$)$_8$CH$_3$ | H | H | −92° (c 2.0) |
| 8 | —CH=CH$_2$ | H | H | −123° (c 0.5) |
| 9 | —CH$_2$—C$_6$H$_5$ | H | H | −98° (c 0.5) |
| 10 | —(CH$_2$)$_2$—C$_6$H$_5$ | H | H | −117° (c 1.0) |

EXAMPLE 11

Production of 3-(2-phenyl-1-propenyl-ONN-azoxy)-2-oxobutane [Compound (I-2): R$_1$=phenyl group, R$_2$=methyl group, R$_3$=H]: (a) To 22 ml of tetrahydrofuran dissolving lithium diisoproylamide therein, said lithium diisoproylamide being prepared from 0.46 ml of diisopropylamine and 3.1 ml of a 1.59N n-buthyl lithium hexane solution in an atmosphere of nitrogen under ice-cooling, was added dropwise 4 ml of tetrahydrofurn solution dissolving 282 mg of the 3-(methyl-ONN-azoxy)-2,2-propylenedioxybutane obtained by Referential Example 1 and the mixture was stirred at 0° C. for thirty minutes. Then 5 ml of tetrahydrofurn solution dissolving 732 ml of acetophenone therein was added to this solution and its stirring was conducted for additional one hour. An aqueous saturated ammonium chloride solution was added to the reaction liquid and an organic layer was extracted with ethyl acetate. This organic layer was washed with water, dried and condensed under vacuum. The residue was purified by means of a silica gel column chromatography thereby to produce 225 mg (yield of 49%) of 3-(2-hydroxy-2-phenylpropyl-ONN-azoxy)-2,2-propylene dioxybutane.

1H-NMR value: δCDCl3, ppm: 0.70, 1.04 (total 3H, each d, J=6.5 Hz), 1.23, 1.36 (total 3H, each s), 1.54, 1.56 (total 3H, each s), 4.36, 4.41 (total 1H, each q), 4.42, 4.55, 4.61 (total 2H, each d, J=13.0 Hz), 5.27 (1H, s).
CHCl3
IR value: γmax, cm$^{-1}$, 1499.

(b) In 3 ml of pyridine was dissolved 140 mg of the 3-(2-hydroxy-2-phenylpropyl-ONN-azoxy)-2,2-propylene dioxybutane obtained by the above (a). Then 0.1 ml of thionyl chloride was added to the mixture under ice-cooling and its stirring was conducted for one hour. The reaction liquid was poured into a glacial water and an organic layer was extracted with benzene and condensed.

The residue was dissolved in 3 ml of toluene and 0.1 ml of 1,8-diazabicyclo [5.4.0]-7-undecene was added to the mixture. Its stirring was conducted at room temperature for one hour. The reaction liquid was purified by means of a preparative silica gel thin-layer chromatography [developing solvent: ether-n-hexane (1:2)] thereby to produce 37 mg (yield of 22%) of 3-(2-phenyl-1-propenyl-ONN-azoxy)-2,2-propylene dioxybutane.

1H-NMR value: δCDCl3, ppm: 1.23 (3H, d, J=6.5 Hz), 1.50 (3H, s), 2.48 (3H, d, J=1.5 Hz), 4.74 (1H, q, J=6.5 Hz), 7.12 (1H, q, J=1.5 Hz),
CHCl3
IR value: γmax, cm$^{-1}$, 1465.

(c) In 1.8 ml of acetone was dissolved 35 mg of the 3-(2-phenyl-1-propenyl-ONN-azoxy)-2,2-propylene dioxybutane obtained by the above (b). Then 35 mg of ferric chloride-silica gel was added to the mixture and its stirring was conducted for one hour. The reaction liquid was purified by means of a silica gel column chromatography [solvent: ether-n-hexane (1:1)] thereby to produce 13 mg (yield of 47%) of the above-captioned object compound.

Specific optically rotation: $[\alpha]_D^{22}$ −65° (c 0.5, CHCl$_3$)

1H-NMR value: δCDCl3, ppm: 1.52 (3H, d, J=6.5 Hz), 2.24 (3H, s), 2.52 (3H, d, J=1.5 Hz), 4.62 (1H, q, J=6.5 Hz), 7.17 (1H, q, J=1.5 Hz),
CHCl3
IR value: γmax, cm$^{-1}$, 1717, 1458

EXAMPLES 12–19

Using the corres. starting compound the reaction and treatment were made as in Example 11, thereby to produce the compound (I-2) shown in Table 3.

TABLE 3

R$_1$R$_3$C=C(R$_2$)—N=N(→O)—CH(CH$_3$)—C(=O)—CH$_3$  (I-2)

| Example No. | R$_1$ | R$_2$ | R$_3$ | $[\alpha]_D^{\prime\prime}$ (CHCl$_3$) |
|---|---|---|---|---|
| 12 | —C$_6$H$_5$ | —CH$_2$CH$_3$ | H | −57° (c 1.0) |
| 13 | " | —(CH$_2$)$_2$CH$_3$ | H | −62° (c 1.0) |
| 14 | " | —(CH$_2$)$_3$CH$_3$ | H | −63° (c 1.0) |
| 15 | —C$_6$H$_4$—Cl | —CH$_3$ | H | −30° (c 0.5) |
| 16 | —C$_6$H$_4$—C$_6$H$_5$ | " | H | −37° (c 1.0) |

TABLE 3-continued $$\begin{array}{c}R_1\\ \phantom{xx}\diagdown\\ \phantom{xxx}C=C\\ \phantom{xx}\diagup\phantom{xxxx}\diagdown\\ R_2\phantom{xxxxx}N=N-CH-\overset{\overset{\displaystyle O}{\|}}{C}-CH_3\\ \phantom{xxxxxx}\downarrow\phantom{xx}|\\ \phantom{xxxxxx}O\phantom{xx}CH_3\end{array}\quad(I-2)$$

| Example No. | $R_1$ | $R_2$ | $R_3$ | $[\alpha]_D^{tt}$ (CHCl$_3$) |
|---|---|---|---|---|
| 17 | Cl-C$_6$H$_3$-Cl | " | H | −71° (c 1.0) |
| 18 | F-C$_6$H$_3$-F | " | H | −64° (c 0.4) |
| 19 | Cl-C$_6$H$_4$- | −(CH$_2$)$_3$CH$_3$ | H | −49° (c 1.0) |

EXAMPLE 20

Production of 3-(1-methyl-1-hexenyl-ONN-azoxy)-2-oxobutane [Compound (I-2): $R_1$=n-butyl group, $R_2$=H, $R_3$=methyl group]: (a) In 2.5 ml of tetrahydrofuran was dissolved 253 mg of the 3-(ethyl-ONN-azoxy)-2,2-propylene dioxybutane obtained by Referential Example 2. To this was added dropwise 1.1 ml of an ice-cooled 1,5M lithium diisoproylamide.tetrahydrofuran complex cyclohexane solution (a product of Aldrich Company) and its stirring was conducted for thirty minutes. Then 0.2 ml of n-valeraldehyde was added to this solution and the mixture was stirred for additional ten minutes. An aqueous saturated ammonium chloride solution was added to the reaction liquid and an organic layer was extracted with ether. This organic layer was washed with water, dried and condensed under vacuum. The residue was purified by means of a silica gel column chromatography [eluate: ethyl acetate-bezene (1:10)] thereby to produce 91 mg (yield of 25%) of 3-(2-hydroxy-1-methylhexyl-ONN-azoxy)-2,2-propylene dioxybutane.

$^1$H-NMR value δCDCl3, ppm: 0.90, 0.91 (total 3H, each br.t, J=7.0 Hz), 1.13, 1.14, 1.15 (total 3H, each d, J=7.0 Hz), 4.20-4.45 (1H, m), 4.57, 4.59, 4.65, 4.69 (total 1H, each q, J=7.0 Hz).

CHCl3

IR value: γmax, cm$^{-1}$, 3430, 1496

(b) In 1 ml of tetrahydrofuran was dissolved 84.6 mg of the 3-(2-hydroxy-1-methylhexyl-ONN-azoxy)-2,2-propylene dioxybutane obtained by the above (a). Then 0.065 ml of triethylamine and 0.035 ml of methanesulfonyl chloride were added to the mixture under ice-cooling and its stirring was conducted for ten minutes. Then 3 ml of an aqueous saturated sodium bicarbonate solution was added to the reaction liquid and the mixture was stirred for ten minutes. And an organic layer was extracted with ether. This organic layer was washed with aqueous saturated sodium bicarbonate solution and an aqueous saturated ammonium chloride solution, dried and condensed under vacuum. There resulted a methanesulfonyl compound.

The resultant methanesulfonyl compound was dissolved in 1 ml of benzene. Then 0.56 ml of 1,8-diazabicyclo [5.4.0]-7-undecene was added to the mixture and its stirring was conducted overnight. Water was added to the reaction liquid and an organic layer was extracted with ether. This organic layer was washed with 0.5N hydrochloric acid and an aqueous saturated sodium bicarbonate solution, dried and condensed under vacuum. The residue was purified by means of a silica gel column chromatography [solvent: ether-n-hexane (1:3)] thereby to produce 48.2 mg (yield of 61%) of 3-(1-hexenyl-ONN-azoxy)-2,2-propylene dioxybutane.

$^1$H-NMR value: δCDCl$_3$, ppm: 0.91 (3H, t, J=7.0 Hz), 1.15 (3H, d, J=6.0 Hz), 1.20-1.50 (4H, m), 1.48 (3H, s), 1.65-1.75 (2H, m), 2.12 (3H, s), 2.18 (2H, q, J=8.0 Hz), 3.85-4.00 (4H, m), 4.75 (1H, q, J=6.0 Hz), 6.76 (1H, t, J=8.0 Hz), CHCl$_3$ IR value: γmax, cm$^{-1}$, 1462 (c).

In 1 ml of acetone was dissolved 43 mg of the 3-(1-hexenyl-ONN-azoxy)-2,2-propylene dioxybutane obtained by the above (b). Then 39 mg of ferric chloride-silica gel was added to the mixture and its stirring was conducted at room temperature for two hours. The reaction liquid was filtered using zeolite and the filtrate was washed with ether and condensed under vacuum. The residue was purified by means of a silica gel column chromatography [solvent: ether-n-hexane (1:5)] thereby to produce 17.6 mg (yield of 53%) of the above-capationed object compound.

$^1$H-NMR value: δCDCl$_3$, ppm: 0.92 (3H, t, J=7.0 Hz), 1.25-1.50 (4H, m), 1.48 (3H, s), 1.65-1.75 (2H, m), 2.12 (3H, s), 2.18 (3H, q, J=8.0 Hz), 3.85-4.00 (4H, m), 4.75 (1H, q, J=6.0 Hz), 6.76 (1H, t, J=8.0 Hz).

CHCl$_3$

IR value: γmax, cm$^{-1}$, 1716, 1456

EXAMPLES 21-27

Using the corres. starting compound the reaction and treatment were made as in Example 20, thereby to produce the compound (I-2) shown in Table 4.

TABLE 4

$$\begin{array}{c}R_1\\ \phantom{xx}\diagdown\\ \phantom{xxx}C=C\\ \phantom{xx}\diagup\phantom{xxxx}\diagdown\\ R_2\phantom{xxxxx}N=N-CH-\overset{\overset{\displaystyle O}{\|}}{C}-CH_3\\ \phantom{xxxxxx}\downarrow\phantom{xx}|\\ \phantom{xxxxxx}O\phantom{xx}CH_3\end{array}\quad(I-2)$$

| Example No. | R1 | R2 | R3 | $[\alpha]_D^{tt}$ (CHCl$_3$) |
|---|---|---|---|---|
| 21 | −(CH$_2$)$_3$CH$_3$ | H | Cl-C$_6$H$_4$- | −38° (c 0.4) |
| 22 | H | −(CH$_2$)$_3$CH$_3$ | " | −66° (c 1.0) |
| 23 | Cl-C$_6$H$_4$- | −CH$_3$ | −CH$_3$ | −48° (c 0.4) |
| 24 | " | " | −(CH$_2$)$_4$CH$_3$ | −43° (c 0.6) |
| 25 | −(CH$_2$)$_3$CH$_3$ | H | " | −63° (c 0.5) |
| 26 | " | H | C$_6$H$_5$- | −49° (c 0.5) |
| 27 | −(CH$_2$)$_5$− | | H | −120° (c 0.3) |

EXAMPLE 28

Production of 2-hydroxyimino-3-[2-(4-(3-iodopropargyl)oxyphenyl)-1-propenyl-ONN-azoxy)-butane [Compound (I-3): $R_1$=methyl group, $R_2$=4-(3-iodopropargyl)oxyphenyl group, $R_3$=hydrogen atom]: (a) In 3 ml of tetrahydrofuran was dissolved 249 mg of the 3-(methyl- ONN-azoxy)-2,2-propylene dioxybutane obtained by Referential Example 1 in an atmosphere of nitrogen. Then 1.15 ml of cyclohexane dissolving 1.7 mmol of lithium diisoproylamide therein was added to this solution and its stirring was conducted for thirty minutes under ice-cooling. To this solution was added 4 ml of a solution of tetrahydrofuran dissolving 358 mg of 4-propargyloxy acetophenone therein and the mixture was stirred for additional thirty minutes under ice-cooling.

Under ice-cooling 5 ml of an aqueous 10% ammonium chloride solution was added to the reaction mixture and the mixture was stirred for five minutes. Then the extraction was conducted with 50 ml of ether. The extraction liquid was washed with saturated saline solution, dried and condensed under vacuum.

Successively, 650 mg of the so obtained oily substance was purified by means of a silica gel column chromatography (eluate: a 50% ether hexane solution) thereby to produce 242 mg (yield of 51%) of a diastereomer mixture (1:1) of 3-[2-hydroxy-2-(4-propargyloxyphenyl) propyl-ONN-azoxy]-2,2-propylene dioxybutane as a colorless oily substance.

Diastereomer (a)

$^1$H-NMR value: $\delta$CDCl$_3$, ppm: 7.42 (2H, d, J=9 Hz), 6.95 (2H, d, J=9 Hz), 5.24 (1H, br, s), 4.67 (2H, d, J=2 Hz), 4.51 (1H, d, J=12 Hz), 4.39 (1H, d, J=12 Hz), 4.35 (1H, q, J=7 Hz), 3.70–3.97 (4H, m), 2.51 (1H, t, J=2 Hz), 1.71–1.87 (1H, m), 1.54 (3H, s), 1.46–1.59 (1H, m), 1.26 (3H, s), 1.07 (3H, d, J=7 Hz)

CHCl$_3$

IR value: $\gamma$max, CHCl$_3$, cm$^{-1}$, 3430 (br), 3290, 1505, 1225 (br)

Diastereomer (b)

$^1$H-NMR value: $\delta$CDCl$_3$, ppm: 7.40 (2H, d, J=9 Hz), 6.93 (2H, d, J=9 Hz), 5.24 (1H, br, s), 4.67 (2H, d, J=2 Hz), 4.57 (1H, d, J=12 Hz), 4.43 (1H, q, J=7 Hz), 4.40 (1H, d, J=12 Hz), 3.77–3.98 (4H, m), 2.50 (1H, t, J=2 Hz), 1.66–1.84 (1H, m), 1.55–1.66 (1H, m), 1.54 (3H, s), 1.36 (3H, s), 0.74 (3H, d, J=7 Hz), IR value: $\gamma$max, CHCl$_3$, cm$^{-1}$, 3420 (br), 3290, 1505, 1225 (br).

(b) In 0.4 ml of pyridine was dissolved 155 mg of the 3-[2-hydroxy-2-(4-propargyloxyphenyl)propyl-ONN-azoxy]-2,2-propylene dioxybutane obtained by the above (a). Then 0.05 ml of thionyl chloride was added to the mixture and its stirring was conducted for fifteen minutes under ice-cooling. Successively, 0.6 ml of 1,8-diazabicyclo[5.4.0]-7-undecen was added to the mixture and its stirring was conducted for additional 1.5 hours under ice-cooling.

Then 50 ml of ether and 5 ml of a 1N hydrochloric acid were added to the reaction liquid and an ether layer was batched off. This layer was washed with 5 ml of saturated saline solution, 5 ml of an aqueous saturated sodium bicarbonate solution and 5 ml of saturated saline solution in order, dried and condensed under vacuum. Then 170 mg of the resultant oily substance was separation formed by means of a silica gel column chromatography (solvent: benzene) thereby to produce 150 mg (yield of 71%) of 3-[2-(4-propargyloxyphenyl)-1-propenyl-ONN-azoxy]-2,2-propylene dioxybutane as a colorless oily substance.

$^1$H-NMR value: $\delta$CDCl$_3$, ppm: 7.33 (2H, d, J=9 Hz), 7.19 (2H, q, J=1 Hz), 6.91 (2H, d, J=9 Hz), 4.66 (1H, q, J=7 Hz), 4.65 (2H, d, J=2 Hz), 3.86–3.93 (4H, m), 2.47 (1H, t, J=2 Hz), 2.38 (3H, d, J=1 Hz), 1.67–1.81 (1H, m), 1.52–1.64 (1H, m), 1.43 (3H, s), 1.15 (3H, d, J=7 Hz), IR value: $\gamma$max, CHCl$_3$, cm$^{-1}$, 3290, 1505, 1225 (br)

(c) In 1.5 ml of methanol was dissolved 63 mg of the 3-[2-(4-propargyloxyphenyl)-1-propenyl-ONN-azoxy]-2,2-propylene dioxybutane obtained by the above (b). Then 0.07 ml of an aqeuous 10M sodium hydroxide solution and 100 mg of iodine were added to the mixture under ice-cooling. After the reaction compound became homogeneous, the reaction mixture was stirred at room temperature for fifteen minutes.

Successively, 50 ml of ether and 5 ml of an aqueous 1M sodium thiosulfate solution were added to the reaction mixture and an ether layer was batched off. This layer was washed with 5 ml of saturated saline solution, dried and condensed under vacuum. Then 83 g of the resultant oily substance was purified by means of a silica gel dispersed thin-film chromatography (solvent: ethyl acetate-benzene (1:5)]thereby to produce 85 mg (yield of 99%) of 3-[2-(4-(3-iodopropargyl) oxyphenyl)-1-propenyl-ONN-azoxy]-2,2-propylene dioxybutane as a colorless oily substance.

$^1$H-NMR value: $\delta$CDCl$_3$, ppm: 7.39 (2H, d, J=9 Hz), 7.12 (1H, q, J=1 Hz), 6.96 (2H, d, J=9 Hz), 4.85 (2H, s), 4.73 (1H, q, J=7 Hz), 3.93–3.99 (4H, m), 2.45 (3H, d, J=1 Hz), 1.50 (3H, s), 1.22 (3H, d, J=7 Hz).

IR value: $\gamma$max, CHCl$_3$, cm$^{-1}$, 1505, 1225 (br).

(d) In 0.5 ml of acetone was dissolved 61 mg of the 3-[2-(4-(3-iodopropargyl)oxyphenyl)-1-propenyl-ONN-azoxy]-2,2-propylene dioxybutane obtained by the above (c). Then 115 mg of iron chloride-silca gel (11 wt. %) was added to the mixture and its stirring was conducted at room temperature for two hours.

Successively, 10 ml of carbon tetrachloride was added to the reaction mixture and the mixture was suction filtered using zeolite. The filtrate was then condensed under vacuum. The resultant oily substance was purified by means of a silica gel column chromatography (solvent: ether-hexane (1:1)] thereby to produce 43 mg (yield of 79 %) of 3-[2-(4-(3-iodopropargyl)oxyphenyl)-1-propenyl-ONN-azoxy]-2-oxobutane [Compound (I-2): $R_1$=methyl group, $R_2$=4-(3-iodopropargyl)oxyphenyl group, $R_3$=hydrogen atom] as a colorless oily substance.

$^1$H-NMR value: $\delta$CDCl$_3$, ppm: 7.41 (2H, d, J=9 Hz), 7.19 (1H, q, J=1 Hz), 6.98 (2H, d, J=9 Hz), 4.86 (2H, s), 4.62 (1H, q, J=7 Hz), 2.50 (3H, d, J=1 Hz), 2.23 (3H, s), 1.51 (3H, d, J=7 Hz).

IR value: $\gamma$max, CHCl$_3$, cm$^{-1}$, 1715, 1505, 1220.

[$\alpha$] $_D^{23}$ −21° (C, 2.9, chloroform)

(e) In 0.3 ml of methanol was dissolved 33.2 mg of the 3-[2-(4-(3-iodopropargyl)oxyphenyl)-1-propenyl-ONN-azoxy]-2-oxobutane obtained by the above (d). Then 11.1 mg of hydroxylamine hydrochloride and 0.02 ml of pyridine were added to the mixture and its stirring was conducted at room temperature for ten minutes.

Successively, 25 ml of ether and 5 ml of water were added to the reaction mixture and an ether layer was batched off. This layer was washed with saturated saline solution, dried and condensed under vacuum. Then 37 mg of the resultant oily substance was purified by means of a silica gel preparative thin-layer chromatography (solvent: ethyl acetate-benzene (1:3)] thereby to produce anti- and syn-isomers on the oxime hydroxyl group of the above-captioned object compound in respective amounts of 11.7 mg (yield of 51%) and 9.2 mg (yield of 27%) as colorless oily substances.

(a) Anti-isomer

1H-NMR value: $\delta CDCl_3$, ppm: 7.40 (2H, d, J=9 Hz), 7.12 (1H, s), 6.97 (2H, d, J=9 Hz), 4.85 (2H, s), 4.82 (1H, q, J=7 Hz), 2.48 (3H, s), 1.97 (3H, s), 1.42 (3H, d, J=7 Hz).

IR value: $\gamma max$, $CHCl_3$, $cm^{-1}$, 3550, 3270 (br), 1605, 1505, 1220 (br).

$[\alpha]_D^{23}$ −17° (C, 2.5, chloroform)

(b) Syn-isomer

1H-NMR value: $\delta CDCl_3$, ppm: 7.41 (2H, d, J=9 Hz), 7.16 (1H, q, J=1 Hz), 6.97 (2H, d, J=9 Hz), 5.40 (1H, q, J=7 Hz), 4.86 (2H, s), 2.51 (3H, d, J=1 Hz), 1.81 (3H, s), 1.45 (3H, d, J=7 Hz).

IR value: $\gamma max$, $CHCl_3$, $cm^{-1}$, 3560, 3240 (br), 1605, 1505, 1225 (br)

$[\alpha]_D^{23}$ 30 84° (C, 1.0, chloroform)

EXAMPLE 29

Production of 2-hydroxyimino-3-[2-(2-(3-iodopropargyl)oxyphenyl)-1-propenyl-ONN-azoxy]-butane [Compound (I-3): $R_1$=methyl group, $R_2$=2-(3-iodopropargyl)oxyphenyl group, $R_3$=hydrogen atom]:

(a) A mixture (1:1) of diastereomers of 3-[2-hydroxy-2-(2-propargyloxyphenyl)-propyl-ONN-azoxy]-2,2-propylene dioxybutane was produced by using the 3-(methyl-ONN-azoxy)-2,2-propylene dioxybutane obtained in Referential Example 1 and 2-propargyloxyacetophenone, reacting both of these and treating the reaction mixture as in Example 28-(a).

Diastereomer (a) (Colorlessoily substance):

1H-NMR value: $\delta CDCl_3$, ppm: 7.70 (1H, dd, J=8, 2 Hz), 7.23 (1H, td, J=8, 2 Hz), 6.99 (1H, t, J=8 Hz), 6.94 (1H, d, J=8 Hz), 5.39 (1H, s), 5.15 (1H, d, J=12 Hz), 4.75 (2H, d, J=2 Hz), 4.45 (1H, d, J=12 Hz), 4.41 (1H, q, J=7 Hz), 3.77–3.88 (2H, m), 3.48–3.57 (1H, m), 3.32–3.42 (1H, m), 2.54 (1H, t, J=2 Hz), 1.59–1.70 (2H, m), 1.61 (3H, s), 1.23 (3H, s), 0.96 (3H, d, J=7 Hz).

IR value: $\gamma max$, $CHCl_3$, $cm^{-1}$, 3430 (br), 3290, 1485, 1225 (br).

Diastereomer (b)

Colorless prism-like crystal (m.p. 127.0° to 130.5° C.)

1H-NMR value: $\delta CDCl_3$, ppm: 7.66 (1H, dd, J=8, 2 Hz), 7.24 (1H, td, J=8, 2 Hz), 6.98 (1H, t, J=8 Hz), 6.94 (1H, d, J=8 Hz), 5.28 (1H, s), 5.23 (1H, d, J=11 Hz), 4.73 (2H, d, J=2 Hz), 4.35 (1H, d, J=11 Hz), 4.36 (1H, q, J=7 Hz), 3.74–3.91 (4H, m), 2.54 (1H, t, J=2 Hz), 1.58–1.72 (2H, m, Hm), 1.63 (3H, s), 1.33 (3H, s), 0.44 (3H, d, J=7 Hz).

IR value: $\gamma max$, $CHCl_3$, $cm^{-1}$, 3440 (br), 3270, 1485, 1385, 1240, 1090.

(b) 3-[2-(2-propargyloxyphenyl)-1-propenyl-ONN-azoxy]-2,2-propylene dioxybutane was obtained as a colorless oily substance by using the 3-[2-hydroxy-2-(2-propargyloxyphenyl)-propyl-ONN-azoxy]-2,2-propylene dioxybutane obtained in the above (a), conducting the reaction and treatment as in Example 28-(b).

1H-NMR value: $\delta CDCl_3$, ppm: 7.32 (1H, ddd, J=8, 7, 2 Hz), 7.21 (1H, dd, J=7, 2 Hz), 7.04 (1H, d, J=8 Hz), 6.99 (1H, t, J=7 Hz), 6.94 (1H, q, J=1 Hz), 4.74 (1H, q, J=7 Hz), 4.73 (2H, d, J=2 Hz), 3.93–3.99 (4H, m), 2.25 (1H, t, J=2 Hz), 2.43 (3H, d, J=1 Hz), 1.60–1.87 (2H, m), 1.50 (3H, s), 1.22 (3H, d, J=7 Hz).

IR value: $\gamma max$, $CHCl_3$, $cm^{-1}$, 3290, 1485, 1450.

(c) 3-[2-(2-(3-iodopropargyl)oxyphenyl)-1-propenyl-ONN-azoxy]-2,2-propylene dioxybutane was obtained as a colorless oily substance by using the 3-[2-(2-propargyloxyphenyl)-propenyl-ONN-azoxy]-2,2-propylene dioxybutane obtained in the above (b), conducting the reaction and treatment as in Example 28-(c).

1H-NMR value: $\delta CDCl_3$, ppm: 7.33 (1H, t, J=7 Hz), 7.21 (1H, d, J=7 Hz), 7.03 (1H, d, J=7 Hz), 6.99 (1H, t, J=7 Hz), 6.94 (1H, s), 4.86 (2H, s), 4.74 (1H, q, J=7 Hz), 3.93–3.99 (4H, m), 2.42 (3H, s), 1.60–1.88 (2H, m), 1.50 (3H, s), 1.22 (3H, d, J=7 Hz).

IR value: $\gamma max$, $CHCl_3$, $cm^{-1}$, 1485, 1450.

(d) 3-[2-(2-(3-iodopropargyl)oxyphenyl)-1-propenyl-ONN-azoxy]-2-oxobutane [Compound (I-2): $R_1$=methyl group, $R_2$=2-(3-iodopropargyl)oxyphenyl group, $R_3$=hydrogen atom] was obtained as a colorless oily substance by using the 3-[2-(2-(3-iodopropargyl)oxyphenyl)-1-propenyl-ONN-azoxy]-2,2-propylene dioxybutane obtained in the above (c), conducting the reaction and treatment as in Example 28-(d).

1H-NMR value: $\gamma CDCl_3$, ppm: 7.35 (1H, ddd, J=8, 7, 2 Hz), 7.21 (1H, dd, J=7, 2 Hz), 7.04 (1H, d, J=8 Hz), 7.01 (1H, t, J=7 Hz), 6.01 (1H, q, J=1 Hz), 4.87 (2H, s), 4.61 (1H, q, J=7 Hz), 2.45 (3H, d, J=1 Hz), 2.23 (3H, s), 1.50 (3H, d, J=7 Hz).

IR value: $\gamma max$, $CHCl_3$, $cm^{-1}$, 1715, 1485, 1450

$[\alpha]_D^{23}$ −37° (C, 3.5, chloroform)

(e) Anti- and syn-isomers on the oxime hydroxyl group of the above-captioned object compound were obtained as colorless oily substances by using the 3-[2-(2-(3-iodopropargyl)oxyphenyl)-1-propenyl-ONN-azoxy]-2-oxobutane obtained in the above (d), conducting the reaction and treatment as in Example 28-(d).

Anti-isomer

1H-NMR value: $\delta CDCl_3$, ppm: 7.33 (1H, ddd, J=8, 7, 2 Hz), 7.20 (1H, dd, J=7, 2 Hz), 7.03 (1H, d, J=8 Hz), 7.00 (1H, t, J=7 Hz), 6.94 (1H, q, J=1 Hz), 4.86 (2H, s), 4.83 (1H, q, J=7 Hz), 2.43 (3H, d, J=1 Hz), 1.98 (3H, s), 1.41 (3H, d, J=7 Hz).

IR value: $\gamma max$, $CHCl_3$, $cm^{-1}$, 3550, 3260 (br), 1485, 1445

$[\alpha]_D^{23}$ +8.0° (C, 0.56, chloroform)

Syn-isomer

1H-NMR value: $\delta CDCl_3$, ppm: 7.34 (1H, ddd, J=8, 7, 2 Hz), 7.21 (1H, dd, J=7, 2 Hz), 7.04 (1H, d, J=8 Hz), 7.01 (1H, t, J=7 Hz), 6.97 (1H, q, J=1 Hz), 5.42 (1H, q, J=7 Hz), 4.87 (2H, s), 2.46 (3H, d, J=1 Hz), 1.83 (3H, s), 1.48 (3H, d, J=7 Hz).

IR value: $\gamma max$, $CHCl_3$, $cm^{-1}$, 3560, 3240 (br), 1485, 1450

$[\alpha]_D^{23}$ +36° (C, 0.25, chloroform)

EXAMPLE 30

Production of 2-hydroxyimino-3-[2-(3-(3-iodopropargyl)oxyphenyl)-1-propenyl-ONN-azoxy]-butane [Compound (I-3): $R_1$32 methyl group, $R_2$=3-(3-iodopropargyl)oxyphenyl group, $R_3$=hydrogen atom]: (a) A mixture (1:1) of diastereomers of 3-[2-hydroxy-2-(3-propargyloxyphenyl)-propyl-ONN-azoxy]-2,2-propylene dioxybutane was produced as an oily substance by using the 3-(methyl-ONN-azoxy)-2,2-propylene dioxybutane obtained in Referential Example 1 and 3-propargyloxyacetophenone, reacting both of these and treating the reaction mixture as in Example 28-(a).

Diastereomer (a):

1H-NMR value: $\delta CDCl_3$, ppm: 7.26 (1H, t, J=8 Hz), 7.16 (1H, br, s), 7.08 (1H, d, J=8 Hz), 6.87 (1H, dd, J=8, 3 Hz), 5.28 (1H, br, s), 4.69 (2H, d, J=2 Hz), 4.54 (1H, d, J=13 Hz), 4.41 (1H, d, J=13 Hz), 4.36 (1H, q, J=7 Hz), 3.69-3.97 (4H, m), 2.52 (1H, t, J=2 Hz), 1.71-1.86 (1H, m), 1.55 (3H, s), 1.48-1.59 (1H, m), 1.26 (3H, s), 1.06 (3H, d, J=7 Hz).

IR value: γmax, CHCl$_3$, cm$^{-1}$, 3430 (br), 3290, 1600, 1500, 1230 (br).

Diastereomer (b)

$^1$H-NMR value: δCDCl$_3$, ppm: 7.25 (1H, t, J=8 Hz), 7.14 (1H, t, J=2 Hz), 7.06 (1H, br, d, J=8 Hz), 6.87 (1H, dd, J=8, 2 Hz), 5.29 (1H, br, s), 4.69 (2H, d, J=2 Hz), 4.59 (1H, d, J=12 Hz), 4.42 (1H, d, J=12 Hz), 4.42 (1H, q, J=7 Hz), 3.77-3.96 (4H, m), 2.52 (1H, t, J=2 Hz), 1.68-1.82 (1H, m), 1.58-1.66 (1H, m), 1.55 (3H, s), 1.36 (3H, s), 0.74 (3H, d, J=7 Hz).

IR value: γmax, CHCl$_3$, cm$^{-1}$, 3420 (br), 3290, 1600, 1500, 1225 (br), (b) 3-[2-(3-propargyloxyphenyl)-1-propenyl-ONN-azoxy]-2,2-propylene dioxybutane was obtained as a colorless oily substance by using the 3-[2-hydroxy-2-(3-propargyloxyphenyl)-propyl-ONN-azoxy)-2,2-propylene dioxybutane obtained in the above (a), conducting the reaction and treatment as in Example 28-(b).

$^1$H-NMR value: δCDCl$_3$, ppm: 7.31 (1H, t, J=8 Hz), 7.12 (1H, q, J=1 Hz), 7.06 (1H, Br, d, J=8 Hz), 7.03 (1H, t, J=2 Hz), 6.98 (1H, dd, J=8, 2 Hz), 4.72 (1H, d, J=2 Hz), 4.72 (1H, q, J=7 Hz), 3.93-4.00 (4H, m), 2.52 (1H, t, J=2 Hz), 2.45 (3H, d, J=1 Hz), 1.74-1.89 (1H, m), 1.60-1.71 (1H, m), 1.51 (3H, s), 1.22 (3H, d, J=7 Hz).

IR value: γmax, CHCl$_3$, cm$^{-1}$, 3290, 1570, 1480, 1220 (br), (c) 3-[2-(3-(3-iodopropargyl)oxyphenyl)-1-propenyl-ONN-azoxy]-2,2-propylene dioxybutane was obtained as a colorless oily substance by using the 3-[2-(3-propargyloxyphenyl)-1-propenyl-ONN-azoxy]-2,2-propylene dioxybutane obtained in the above (b), conducting the reaction and treatment as in Example 28-(c).

$^1$H-NMR value: δCDCl$_3$, ppm: 7.31 (1H, t, J=8 Hz), 7.12 (1H, q, J=1 Hz), 7.07 (1H, br, d, J=8 Hz), 7.01 (1H, t, J=2 Hz), 6.96 (1H, dd, J=8, 2 Hz), 4.85 (2H, s), 4.73 (1H, q, J=7 Hz), 3.93-3.99 (4H, m), 2.45 (3H, d, J=1 Hz), 1.74-1.89 (1H, m), 1.61-1.71 (1H, m), 1.51 (3H, s), 1.22 (3H, d, J=7 Hz), IR value: γmax, CHCl$_3$, cm$^{-1}$, 1575, 1480, 1215 (br).

(d) 3-[2-(3-(3-iodopropargyl)oxyphenyl)-1-propenyl-ONN-azoxy]-2-oxobutane [Compound (I-2): R$_1$=methyl group, R$_2$=3-(3-iodopropargyl)oxyphenyl group, R$_3$=hydrogen atom] was obtained as an oily substance by using the 3-[2-(3-(3-iodopropargyl)oxyphenyl)-1-propenyl-ONN-azoxy)-2,2-propylene dioxybutane obtained in the above (c), conducting the reaction and treatment as in Example 28-(d).

$^1$H-NMR value: δCDCl$_3$, ppm: 7.33 (1H, t, J=8 Hz), 7.18 (1H, q, J=1 Hz), 7.08 (1H, br, d, J=8 Hz), 7.02 (1H, t, J=2 Hz), 6.99 (1H, dd, J=8, 2 Hz), 4.85 (2H, s), 4.62 (1H, q, J=7 Hz), 2.50 (3H, d, J=1 Hz), 2.24 (3H, s), 1.52 (3H, d, J=7 Hz).

IR value: γmax, CHCl$_3$, cm$^{-1}$, 1715, 1595, 1440 (br), 1285

[α]$_D^{23}$ −30° (C, 1.7, chloroform)

(e) Anti- and syn-isomers on the oxime hydroxyl group of the above-captioned object compound were obtained as colorless oily substances respectively by using the 3-[2-(3-(3-iodopropargyl)oxyphenyl)-1-propenyl-ONN-azoxy]-2-oxobutane obtained in the above (d), conducting the reaction and treatment as in Example 28-(e).

Anti-isomer $^1$H-NMR value: δCDCl$_3$, ppm: 7.32 (1H, t, J=8 Hz), 7.12 (1H, br, s), 7.06 (1H, d, J=8 Hz), 7.01 (1H, br, s), 6.97 (1H, d, J=8 Hz), 4.85 (2H, s), 4.83 (1H, q, J=7 Hz), 2.47 (3H, s), 1.98 (3H, s), 1.42 (3H, d, J=7 Hz).

IR value: γmax, CHCl$_3$, cm$^{-1}$, 3550, 3270 (br), 1695, 1465, 1285,

[α]$_D^{23}$ +7.1° (C, 0.68, chloroform)

Syn-isomer $^1$H-NMR value: δCDCl$_3$, ppm: 7.33 (1H, t, J=8 Hz), 7.16 (1H, q, J=1 Hz), 7.08 (1H, br, d, J=8 Hz), 7.02 (1H, t, J=2 Hz), 6.98 (1H, dd, J=8, 2 Hz), 5.41 (1H, q, J=7 Hz), 4.86 (2H, s), 2.51 (3H, d, J=1 Hz), 1.83 (3H, s), 1.46 (3H, d, J=7 Hz).

IR value: γmax, CHCl$_3$, cm$^{-1}$, 3560, 3240 (br), 1600, 1460, 1285.

[α]$_D^{23}$ +67° (C, 0.19, chloroform)

EXAMPLE 31

Production of 2-hydroxyimino-3-[2-(4-(3-iodopropargyl)oxyphenyl)-vinyl-ONN-azoxy)-butane [Compound (I-3): R$_1$=hydrogen atom, R$_2$=4-(3-iodopropargyl)oxyphenyl group, R$_3$=hydrogen atom]: (a) A mixture (4:5) of diastereomers of 3-[2-hydroxy-2-(4-propargyloxyphenyl)-ethyl-ONN-azoxy]-2,2-propylene dioxybutane was produced as a colorless oily substance by using 743 mg of the 3-(methyl-ONN-azoxy)-2,2-propylene dioxybutane obtained in Referential Example 1 and 1.08 g of 4-propargyloxybenzaldehyde, reacting both of these and treating the reaction mixture as in Example 28-(a).

Diastereomer (a):

$^1$H-NMR value: δCDCl$_3$, ppm: 7.35 (2H, d, J=9 Hz), 6.99 (2H, d, J=9 Hz), 5.32 (1H, br, d, J=8 Hz), 4.70 (2H, d, J=2 Hz), 4.54 (1H, dd, J=13, 2 Hz), 4.36 (1H, dd, J=13, 8 Hz), 4.32 (1H, br, s), 3.91-4.06 (2H, m), 3.86 (1H, q, J=7 Hz), 3.74-3.86 (2H, m), 2.52 (1H, t, J=2 Hz), 1.87-2.06 (1H, m), 1.47 (3H, s), 1.34-1.44 (1H, m), 1.19 (3H, d, J=7 Hz).

IR value: γmax, CHCl$_3$, cm$^{-1}$, 3410 (br), 3240, 1495, 1220 (br), 1155.

Diastereomer (b):

$^1$H-NMR value: δCDCl$_3$, ppm: 7.36 (2H, d, J=9 Hz), 6.98 (2H, d, J=9 Hz), 5.32 (1H, br, d, J=9 Hz), 4.69 (2H, d, J=2 Hz), 4.51 (1H, dd, J=13, 9 Hz), 4.48 (1H, br, s), 4.27 (1H, dd, J=13, 2 Hz), 3.92-4.06 (2H, m), 3.96 (1H, q, J=6 Hz), 3.77-3.87 (2H, m), 2.51 (1H, t, J=2 Hz), 1.89-2.07 (1H, m), 1.50 (3H, s), 1.33-1.45 (1H, s), 1.20 (3H, d, J=6 Hz).

IR value: γmax, CHCl$_3$, cm$^{-1}$, 3390 (br), 3300, 1495, 1220 (br), 1155

(b) There was obtained 239 mg (yield of 56%) of 3-[2-(4-propargyloxyphenyl)-vinyl-ONN-azoxy]-2,2-propylene dioxybutane as a colorless oily substance by using 449 mg of the 3-[2-hydroxy-2-(4-propargyloxyphenyl)-ethyl-ONN-azoxy]-2,2-propylene dioxybutane obtained in the above (a), conducting the reaction and treatment as in Example 28-(b).

$^1$H-NMR value: δCDCl$_3$, ppm: 7.76 (1H, d, J=14 Hz), 7.57 (1H, d, J=14 Hz), 7.45 (2H, d, J=9 Hz), 6.99 (2H, d, J=9 Hz), 4.73 (2H, d, J=2 Hz), 4.71 (1H, q, J=7 Hz), 3.92-4.02 (4H, m), 2.55 (1H, t, J=2 Hz), 1.77-1.92 (1H, m), 1.61-1.69 (1H, m), 1.51 (3H, m), 1.22 (3H, d, J=7 Hz).

IR value: γmax, CHCl$_3$, cm$^{-1}$, 3290, 1605, 1510, 1450, 1230 (br).

(c) There was obtained 277 mg (yield of 88%) of 3-[2-(4-(3-iodopropargyl)oxyphenyl-vinyl-ONN-azoxy]-2,2-propylene dioxybutane as a colorless oily substance by using 229 mg of the 3-[2-(4-propargyloxyphenyl)-vinyl-ONN-azoxy]-2,2-propylene dioxybutane obtained in the above (b), conducting the reaction and treatment as in Example 28-(c).

$^1$H-NMR value: δCDCl$_3$, ppm: 7.76 (1H, d, J=14 Hz), 7.57 (1H, d, J=14 Hz), 7.45 (2H, d, J=9 Hz), 6.97 (2H, d, J=9 Hz), 4.86 (2H, s), 4.71 (1H, q, J=6 Hz), 3.90–4.01 (4H, m), 1.77–1.92 (1H, m), 1.57–1.68 (1H, m), 1.51 (3H, s), 1.22 (3H, d, J=6 Hz).

IR value: γmax, CHCl$_3$, cm$^{-1}$, 1605, 1505, 1450, 1225 (br).

(d) There was obtained 225 mg of a crude oily substance of 3-[2-(4-(3-iodopropargyl)oxyphenyl)-vinyl-ONN-azoxy]-2-oxobutane [Compound (I-2):R$_1$=hydrogen atom, R$_2$=4-(3-iodopropargyl)oxyphenyl group, R$_3$=hydrogen atom] by using 249 mg of the 3-[2-(4-(3-iodopropargyl)oxyphenyl)-vinyl-ONN-azoxy]-2,2-propylene dioxybutane obtained in the above (c), conducting the reaction and treatment as in Example 28-(d).

By recrystallizing this crude oily substance with methanol was obtained a yellowish needle-like crystal having a melting point of 86° C. (degradation).

$^1$H-NMR value: δCDCl$_3$, ppm: 7.79 (1H, d, J=14 Hz), 7.58 (1H, d, J=14 Hz), 7.47 (2H, d, J=9 Hz), 6.99 (2H, d, J=9 Hz), 4.87 (2H, s), 4.68 (1H, q, J=7 Hz), 2.21 (3H, s), 1.51 (3H, d, J=7 Hz).

IR value: γmax, CHCl$_3$, cm$^{-1}$, 1715, 1600, 1510, 1375, 1300, 1250, 1170.

(e) Anti- and syn-isomers on the oxime hydroxyl group of the above-captioned object compound were obtained as colorless oily substances in respective amounts of 136 mg and 52 mg by using 225 mg of the crude oily substance of the 3-[2-(4-(3-iodopropargyl)oxyphenyl)-vinyl-ONN-azoxy]-2-oxobutane obtained in the above (d), conducting the reaction and treatment as in Example 28-(e).

Anti-isomer $^1$H-NMR value: δCDCl$_3$, ppm: 7.77 (1H, d, J=14 Hz), 7.52 (1H, d, J=14), 7.46 (2H, d, J=9 Hz), 6.98 (2H, d, J=9 Hz), 4.87 (1H, q, J=7 Hz), 4.86 (2H, s), 1.98 (3H, s), 1.42 (3H, d, J=7 Hz).

IR value: γmax, CHCl$_3$, cm$^{-1}$, 3550, 3260 (br), 1605, 1505, 1455, 1220 (br), 1170.

[α]$_D^{23}$ +21° (C, 1.2, chloroform).

Syn-isomer $^1$H-NMR value: δCDCl$_3$, ppm: 7.79 (1H, d, J=14 Hz), 7.53 (1H, d, J=14), 7.47 (2H, d, J=9 Hz), 6.98 (2H, d, J=9 Hz), 5.43 (1H, q, J=7 Hz), 4.87 (2H, s), 1.79 (3H, s), 1.46 (3H, d, J=7 Hz).

IR value: γmax, CHCl$_3$, cm$^{-1}$, 3550, 3260 (br), 1605, 1505, 1455, 1220 (br), 1170.

[α]$_D^{23}$ +44° (C, 0.63, chloroform).

EXAMPLE 32

Production of 3-[2-(2-chlorophenyl)-vinyl-ONN-azoxy]-2-hydroxyiminobutane [Compound (I-3): R$_1$=hydrogen atom, R$_2$=2-chlorophenyl group, R$_3$=hydrogen atom]: (a) There was obtained 463 mg (yield of 84%) of 3-[2-(2-chlorophenyl)-2-hydroxyethyl-ONN-azoxy]-2,2-propylene dioxybutane by using 297 mg of the 3-(methyl-ONN-azoxy)-2,2-propylene dioxybutane obtained in Referential Example 1 and 0.36 ml of O-chlorobenzaldehyde (VI), reacting both of these and treating the reaction mixture as in Example 28-(a).

$^1$H-NMR value: δCDCl$_3$, ppm: 1.06 (3H, d, J=6.34 Hz), 1.28 (3H, d, J=6.59 Hz), 1.46 (3H, s), 1.48 (1H, s), 1.92–2.05 (4H), 3.76–4.90 (16H), 5.62–5.68 (2H), 7.24–7.77 (8H).

(b) There was obtained 222 mg (yield of 82.3%) of 3-[2-(2-chlorophenyl)-vinyl-ONN-azoxy]-2,2-propylene dioxybutane by using 285 mg of the 3-[2-(2-chlorophenyl)-2-hydroxyethyl-ONN-azoxy]-2,2-propylene dioxybutane obtained in the above (a), conducting the reaction and treatment as in Example 28-(b).

$^1$H-NMR value: δ-CDCl$_3$, ppm: 1.23 (3H, d, J=6.35 Hz), 1.51 (3H, s), 1.62–1.87 (2H), 3.94–4.01 (4H), 4.71 (1H, q, J=6.35 Hz), 7.25–7.56 (4H), 7.94 (2H, q, J=13.67 Hz), IR value: γmax, CHCl$_3$, cm$^{-1}$, 1460, UV (EtOH, λmax)[nm], 276.

[α]$_D^{22}$ +34.4° (C, 1.0, CHCl$_3$).

(c) A crude oily substance was obtained by using 32 g of the 3-[2-(2-chlorophenyl)-vinyl-ONN-azoxy]-2,2-propylene dioxybutane obtained in the above (b), conducting the reaction and treatment as in Example 28-(d). There was obtained 18.3 mg (yield of 66.2%) of the above-captioned object compound as a mixture (3:1) of anti- and syn-isomers by conducting the reaction and treatment as in Example 28-(e) without purifying this crude oily substance.

$^1$H-NMR value: δCDCl$_3$, ppm: 1.43 (3H, d, J=6.84 Hz), 1.47 (3H, d, J=7.33 Hz), 1.82 (3H, s), 1.99 (3H, s), 4.88 (1H, q, J=6.84 Hz), 7.29–7.63 (10 H, s), 8.18–8.23 (2 H, s), IR value: γmax, CHCl$_3$, cm$^{-1}$14658.

EXAMPLE 33

Production of 3-[2-(2-chlorophenyl)-1-propenyl-ONN-azoxy]-2-hydroxyimino butane [Compound (I-3): R$_1$=methyl group, R$_2$=2-chlorophenyl group, R$_3$=hydrogen atom]: (a) There was obtained 194 mg (yield of 33%) of 3-[2-(2-chlorophenyl)-2-hydroxypropyl-ONN-azoxy]-2,2-propylene dioxybutane by using 320 mg of the 3-(methyl-ONN-azoxy)-2,2-propylene dioxybutane obtained in Referential Example 1 and 0.45 ml of O-chloroacetophenone, reacting both of these and treating the reaction mixture as in Example 28-(a).

$^1$H-NMR value: δCDCl$_3$, ppm: 0.46 (3H, d, J=6.35 Hz), 1.01 (3H, d, J=6.35 Hz), 1.17 (3H, s), 1.36 (3H, s), 1.71 (3H, s), 1.72 (3H, s), 1.45–1.80 (4H), 3.65–3.85 (8H), 4.25 (1H, q, J=6.35 Hz), 4.34 (1H, q, J=6.35 Hz), 4.42 (1H, d, J=12.21 Hz), 4.53 (1H, d, J=12.7 Hz), 5.31 (1H, d, J=12.7 Hz), 5.43 (1H, d, J=12.2 Hz), 5.52 (1H, s), 5.66 (1H, s), 7.19–7.22 (6H), 7.84–7.90 (2H), (b) There was obtained 34.9 mg (yield of 20%) of 3-[2-(2-chlorophenyl)-1-propenyl-ONN-azoxy]-2,2-propylene dioxybutane by using 184 mg of the 3-[2-(2-chlorophenyl)-2-hydroxypropyl-ONN-azoxy]-2,2-propylene dioxybutane obtained in the above (a), conducting the reaction and treatment as in Example 28-(b).

$^1$H-NMR value: δCDCl$_3$, ppm: 1.22 (3H, d, J=6.35 Hz), 1.50 (3H, s), 2.45 (3H, d, J=1.95 Hz), 3.93–3.99 (4H), 4.71 (1H, q, J=6.35 Hz), 6.88 (1H, d, J=1.95 Hz), 7.24–7.42 (4H).

IR value: γmax, CHCl$_3$, cm$^{-1}$, 1470.

UV (EtOH, λmax) [nm] 233.

[α]$_D^{23}$ +26.4° (C, 1.0, CHCl$_3$), (c) A crude oily substance [compound (I-2)] was obtained by using 27.4 mg of the 3-[2-(2-chlorophenyl)-1-propenyl-ONN-azoxy]-2,2-propylene dioxybutane obtained in the above (b), conducting the reaction and treatment as in Example 28-(d).

There was obtained 18.5 mg (yield of 77.8%) of the above-captioned object compound as a mixture (4:1) of anti- and syn-isomers by conducting the reaction and treatment as in Example 28-(e) without purifying this crude oily substance.

$^1$H-NMR value: $\delta$CDCl$_3$, ppm: 1.42 (3H, d, J=6.35 Hz), 1.44 (3H, d, J=6.70 Hz), 1.83 (3H, s), 1.98 (3H, s), 2.45 (3H, d, J=1.95 Hz), 2.48 (3H, d, J=1.95 Hz), 4.83 (1H, q, J=6.35 Hz), 5.43 (1H, q, J=6.70 Hz), 6.88 (1H, d, J=1.95 Hz), 6.90 (1H, d, J=1.95 Hz), 7.25–7.43 (8H).

IR value: $\gamma$max, CHCl$_3$, cm$^{-1}$, 1463.

EXAMPLE 34

Production of 3-[2-(2,4-difluorophenyl)-1-propenyl-ONN-azoxy]-2-hydroxyimino butane [Compound (I): R$_1$=methyl group, R$_2$=2,4-difluorophenyl group, R$_3$=hydrogen atom]:

(a) There was obtained 419.4 mg (yield of 74.2%) of 3-[2-(2,4-difluorophenyl)-2-hydroxypropyl-ONN-azoxy]-2,2-propylene dioxybutane by using 309 mg of the 3-(methyl-ONN-azoxy)-2,2-propylene dioxybutane obtained in Referential Example 1 and 0.5 ml of 2,4-difluoroacetophenone, reacting both of these and treating the reaction mixture as in Example 28-(a).

(b) There was obtained 65.4 mg (yield of 16.5%) of 3-[2-(2,4-difluorophenyl)-1-propenyl-ONN-azoxy]-2,2-propylene dioxybutane by using 419 mg of the 3-[2-(2,4-difluorophenyl)-2-hydroxypropyl-ONN-azoxy]-2,2-propylene dioxybutane obtained in the above (a), conducting the reaction and treatment as in Example 28-(b).

(c) There was obtained 38.8 mg (yield of 68.8%) of the above-captioned object compound as a mixture (2:1) of anti- and syn-isomers by conducting the reaction and treatment as in Example 28-(d).

$^1$H-NMR value: $\delta$CDCl$_3$, ppm: 1.42 (3H, d, J=6.84 Hz), 1.45 (3H, d, J=6.84 Hz), 1.83 (3H, s), 1.98 (3H, s), 2.44 (3H, d, J=1.95 Hz), 2.47 (3H, d, J=1.95 Hz), 4.83 (1H, q, J=6.84 Hz), 5.41 (1H, q, J=6.84 Hz), 6.87 (1H, d, J=1.95 Hz), 6.84–7.30 (6H, s).

IR value: $\gamma$max, CHCl$_3$, cm$^{-1}$, 1464

FORMULATION EXAMPLE 1

| (Capsules for administration to humans) | |
|---|---|
| Compound in EXAMPLE 28 | 500 g |
| Microcrystal cellulose | 90 |
| Talc | 30 |

The above components were uniformly mixed in a usual manner and the mixture was filled in 1000 No. O capsules.

FORMULATION EXAMPLE 2

| (Cream for administration to humans) | |
|---|---|
| Compound in EXAMPLE 31 | 2.0 g |
| White soft paraffin | 25.0 |
| Stearyl alcohol | 25.0 |
| Propylene glycol | 12.0 |
| Sodium lauryl sulfate | 1.5 |
| Ethyl p-hydroxybenzoate | 0.5 |
| Deionized water | 34.0 |

The above components were uniformly mixed in a usual manner and the mixture was formed into a cream.

FORMULATION EXAMPLE 3

| (Emulsifiable concentrate for agricultural and horticultural use) | |
|---|---|
| Compound in EXAMPLE 31 | 250 g |
| Epoxidized vegetable oil | 25 |
| Mixture of alkylaryl sulfonate, polyglycol ether and aliphatic alcohol | 100 |
| Dimethylformamide | 50 |
| Xylene | 575 |

The above components were uniformly mixed in a usuall manner and the mixture was formed into an emulsifiable concentrate. This is diluted with water into an emulsion.

INDUSTRIAL AVAILABILITY

The compounds in this invention are excellent in antifungal activity to fungi that infect warm-blooded animals including humans and agricultural and horticultural crops and in stability, and are useful as agents for prevention, treatment or therapy of infectious diseases caused by these fungi or control of plant diseases caused by these fungi.

What we claim is:

1. A compound of the formula $$\begin{array}{c} R_{11} \\ \phantom{R_{11}} \diagdown \\ \phantom{xx} C=C \\ \phantom{R_{11}} \diagup \phantom{xx} \diagdown \\ R_{21} \phantom{xxxx} N=N-CH-\overset{NOH}{\underset{\phantom{x}}{\overset{\|}{C}}}-CH_3 \\ \phantom{xxxxx} \downarrow \phantom{xxx} | \\ \phantom{xxxxxxx} O \phantom{xx} CH_3 \end{array}$$ (I-1)

in which one of R$_{11}$ and R$_{21}$ is a group of formula

[benzene ring]—O—CH$_2$—C≡C—I and the other is a hydrogen atom.

2. The compound which is 2-hydroxyimino-3-[2-(4-(3-iodopropargyl)oxyphenyl)-1-vinyl-ONN-azoxy]-butane.

* * * * *